United States Patent
Qian et al.

(10) Patent No.: US 11,787,817 B2
(45) Date of Patent: Oct. 17, 2023

(54) ALBOFUNGIN AND ITS DERIVATIVES SPECIFICALLY RECOGNIZE HIV-1 LTR-III G-QUADRUPLEX

(71) Applicants: The Hong Kong University of Science and Technology, Hong Kong (CN); Southern Marine Science and Engineering Guangdong Laboratory (Guangzhou), Guangzhou (CN)

(72) Inventors: Peiyuan Qian, Hong Kong (CN); Aifang Cheng, Hong Kong (CN); Changdong Liu, Hong Kong (CN); Wenkang Ye, Hong Kong (CN); Guang Zhu, Hong Kong (CN)

(73) Assignees: The Hong Kong University of Science and Technology, Hong Kong (CN); Southern Marine Science and Engineering Guangdong Laboratory (Guangzhou), Guangzhou (CN)

( * ) Notice: Subject to any disclaimer, the term of this patent is extended or adjusted under 35 U.S.C. 154(b) by 0 days.

(21) Appl. No.: 17/804,979

(22) Filed: Jun. 1, 2022

(65) Prior Publication Data
US 2023/0057842 A1    Feb. 23, 2023

Related U.S. Application Data

(60) Provisional application No. 63/195,192, filed on Jun. 1, 2021.

(51) Int. Cl.
| | |
|---|---|
| *C07D 491/052* | (2006.01) |
| *C07D 491/16* | (2006.01) |
| *A61K 31/436* | (2006.01) |
| *A61P 31/18* | (2006.01) |

(52) U.S. Cl.
CPC ................. *C07D 491/16* (2013.01)

(58) Field of Classification Search
CPC .............. C07D 491/052; C07D 491/16; A61K 31/436; A61P 31/18
See application file for complete search history.

(56) References Cited

FOREIGN PATENT DOCUMENTS

WO      WO-0195909 A1 * 12/2001 ......... A61K 31/4741

OTHER PUBLICATIONS

Bunyapaiboonsri et al., Polycyclic Tetrahydroxanthones From *Streptomyces* Chrestomyceticus BCC24770, Tetrahedron, vol. 72, No. 5, pp. 775-778 (Year: 2016).*
Perrone, R., et al., "Anti-HIV-1 activity of the G-quadruplex ligand BRACO-19," Journal of Antimicrobial Chemotherapy, 2014, 69:3248-3258.
Mitrasinovic, P.M., et al., "Structural Insights into the Binding of Small Ligand Molecules to a G-Quadruplex DNA Located in the HIV-1 Promoter," Journal of Biomolecular Structure and Dynamics, 2017, pp. 1-19.
Ruggiero, E., et al., "G-quadruplexes and G-quadruplex ligands: targets and tools in antiviral therapy," Nucleic Acids Research, 2018, 46(7):3270-3283.
Butovskaya, E., et al.,. "Major G-Quadruplex Form of HIV-1 LTR Reveals a (3 + 1) Folding Topology Containing a Stem-Loop," Journal of the American Chemical Society, 2018, 140:13654-13662.

* cited by examiner

*Primary Examiner* — Brenda L Coleman
(74) *Attorney, Agent, or Firm* — Saliwanchik, Lloyd & Eisenschenk

(57) ABSTRACT

The subject invention pertains to compositions comprising albofungin and/or derivatives thereof, including, chloroalbofungin, 477-albo, 492-albo, 505-albo, 506-1-albo, 506-2-albo, 519-albo, and 562-albo. The subject invention further pertains to methods of treating a subject with HIV using albofungin and/or derivatives thereof, including, chloroalbofungin, 477-albo, 492-albo, 505-albo, 506-1-albo, 506-2-albo, 519-albo, and 562-albo.

12 Claims, 16 Drawing Sheets

Specification includes a Sequence Listing.

477-Albo

492-Albo

505-Albo 506-1-Albo 506-2-Albo

519-Albo

Albofungin

Chloroalbofungin

562-Albo

CD spectra of different types of G4s

CD spectra

Hybrid form ⟶ Parallel form

ALBOFUNGIN AND ITS DERIVATIVES SPECIFICALLY RECOGNIZE HIV-1 LTR-III G-QUADRUPLEX

CROSS-REFERENCE TO RELATED APPLICATION

This application claims the benefit of U.S. Provisional Application Ser. No. 63/195,192, filed Jun. 1, 2021, which is hereby incorporated by reference in its entirety including any tables, figures, or drawings.

BACKGROUND OF THE INVENTION

The full name of AIDS is Acquired Immunodeficiency Syndrome, and it is caused by infection of a retrovirus called Human Immunodeficiency Virus (HIV). Two types of HIV exist, HIV-1 and HIV-2; HIV-1 is much more virulent and infective. After infection, HIV destroys the human immune system, making the human body extremely susceptible to many diseases, and the infected human can die from various health complications. According to estimates by the WHO and UNAIDS, as of the end of 2018, there were approximately 37.9 million people living with HIV worldwide (1), and this number is increasing every year. An HIV infection is incurable, and the patient can only use drugs to suppress the virus in the body to a low level and need to be treated for life, so control costs are high.

After HIV infects host cells, it needs to replicate its genome to produce more viral copies. The replication process involves multiple essential steps (2). Generally, firstly, HIV virion needs to enter the cell to start its replication cycle. After fusion, it injects its RNA into the host cell, and then the viral RNA is reverse-transcribed to DNA under the action of reverse transcriptase. Then viral DNA enters the nucleus of the host cell and is integrated into the host genome by the action of integrase, turning the host cell into the factory to transcribe various viral mRNA and translate various viral protein synthesis. After that, viral RNA and protein assembly and mature within the host cell to form the embryonic form of progeny virus particles. After the modification of protease, the mature HIV virions are able to infect other cells.

Theoretically, HIV cannot replicate if any step of this replication process is interrupted. Therefore, every critical step of the viral cycle is an important target for the development of therapeutic drugs. The research and development of anti-HIV drugs mainly focuses on how to block the replication of the virus. Currently, the most widely used drugs are reverse transcriptase inhibitors and protease inhibitors (3). The former includes Efavirenz, Rilpivirine, and Tenofovir, while the latter includes Darunavir and Lopinavir (4). Although the treatment regimens have greatly extended the life expectancy and improved the quality of life of HIV-infected patients, side effects are also obvious. First, there are many toxic side effects and adverse reactions (5); second, the complex interactions between drugs limit the use of other medicines for infected patients (6); third, drug resistance is a common problem in many of the antivirus drugs (7).

G-quadruplexes (G4s) are non-canonical conformations formed in Guanine-rich regions of nucleic acids (8). Unlike classical Watson-Crick base pairing of double-stranded DNA, four contiguous guanines can form a square planar structure called G-quartet via Hoogsteen-type hydrogen bonds; two or more quartets can stack layer by layer, constituting the G4 structural backbone. G4s have been extensively found not only in the human genome but also in bacteria and viruses (9). Viral G4s play important roles in both key viral processes and viral latency (10). As potential drug candidates, G4s ligands have been developed and screened as powerful tools to study the complexity of G4-mediated mechanisms in the viral life cycle (11, 12), especially G4s found in the unique long terminal repeat (LTR) promoter of HIV-1 (13, 14). It was reported that LTR G4s act as repressor elements of viral transcription initiation (15). Accumulative evidence revealed the presence of three overlapping and thus mutually exclusive G4s within LTR G-rich sequence in the presence of physiological concentrations of $K^+$ (15), named LTR-II, LTR-III and LTR-IV. However, only LTR-III is the predominant structure. Furthermore, bacterial secondary metabolites have always been great sources of antiviral compounds (16), considering their complexity, specificity, and novelty.

Therefore, there is an urgent need for compounds to treat HIV infections.

BRIEF SUMMARY OF THE INVENTION

The subject invention pertains to compositions comprising albofungin and/or derivatives thereof and methods of using said compositions to treat HIV. In certain embodiments, the derivatives of albofungin include, for example, chloroalbofungin, 477-albo, 492-albo, 505-albo, 506-1-albo, 506-2-albo, 519-albo, and 562-albo. Albofungin and/or derivatives thereof can selectively bind to HIV-1 LTR III G4 with limited binding to HIV-1 LTR II G4, HIV-1 LTR IV G4, and human telomeric variant htel21_T18 (d[$(GGGTTA)_2$ GGGTTTGGG]) (SEQ ID NO: 1). Moreover, albofungin and/or its derivatives can exhibit a stronger binding affinity to LTR III G4 than that of RNA binding protein hnRNP A2. In certain embodiments, albofungin can have poor solubility in the solvents' system, which implies a stable and tight binding. Intriguingly, albofungin's monochlorinated product, chloroalbofungin, may not exhibit binding activity even at a high concentration.

The compositions of the subject invention can further be used in methods to treat an HIV infection. Albofungin and its several novel derivatives exhibit specific strong binding affinities to HIV-1 LTR III G-quadruplex but not HIV-1 LTR II G4 and HIV-1 LTR IV G4. The binding of albofungin and its several novel derivatives can stabilize the HIV-1 LTR III G-quadruplex and inhibit the replication of HIV.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. Albofungin producing strain, *Streptomyces chrestomyceticus* BCC 24770 on a GYM agar plate. FIG. 1B. HPLC spectrum of the isolated fractions under 210 nm. FIG. 1C. UV absorption spectrum of albofungin, which is almost identical to all derivatives. FIG. 1D. Enlarged HPLC spectrum clearly shows retention times of different compounds.

FIG. 14A: parallel; FIG. 14B: anti-parallel; FIG. 14C: hybrid conformation, etc.

BRIEF DESCRIPTION OF THE SEQUENCES

Figure 1A:
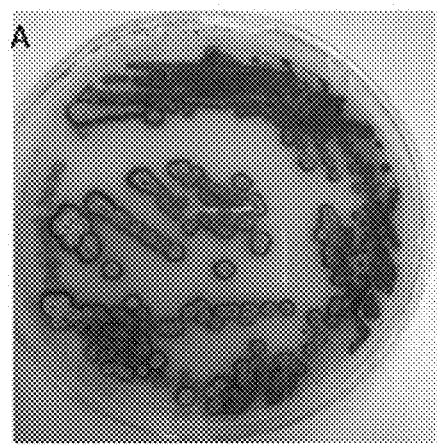
FIGS. 1A-1D. HPLC analysis of the crude extracts of *Streptomyces chrestomyceticus* BCC 24770.
Figure 1B:
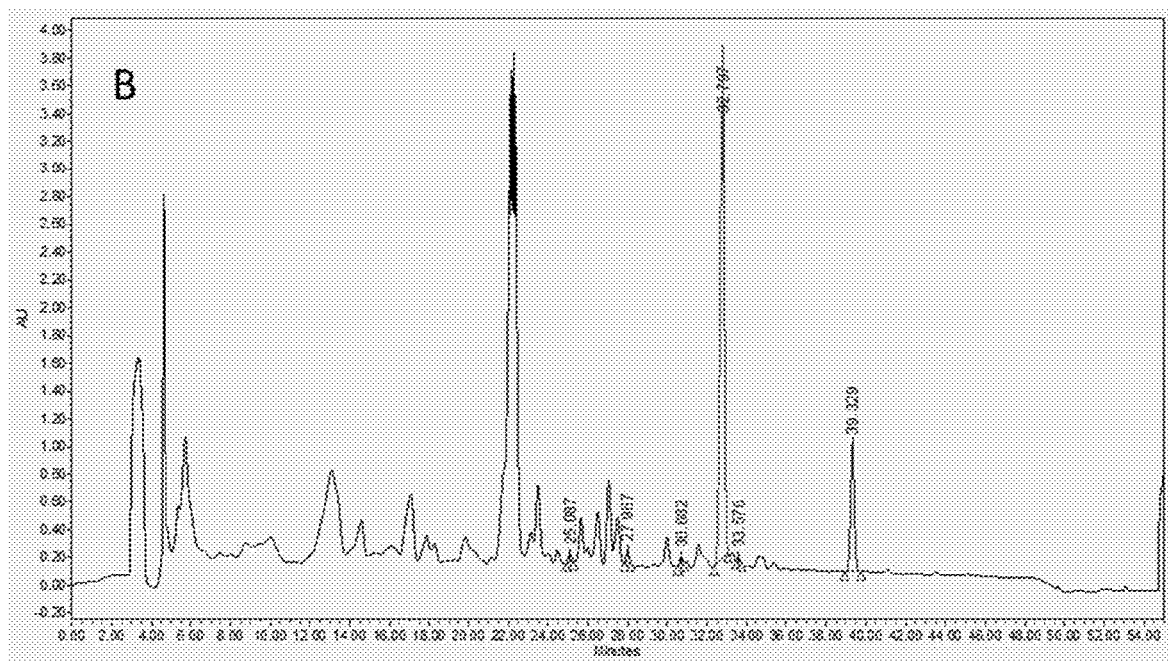
Figure 1C:
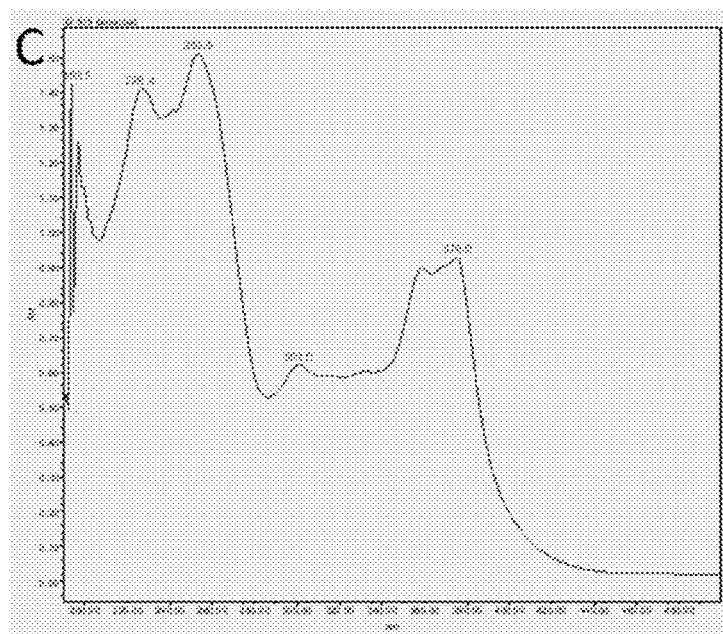
Figure 1D:
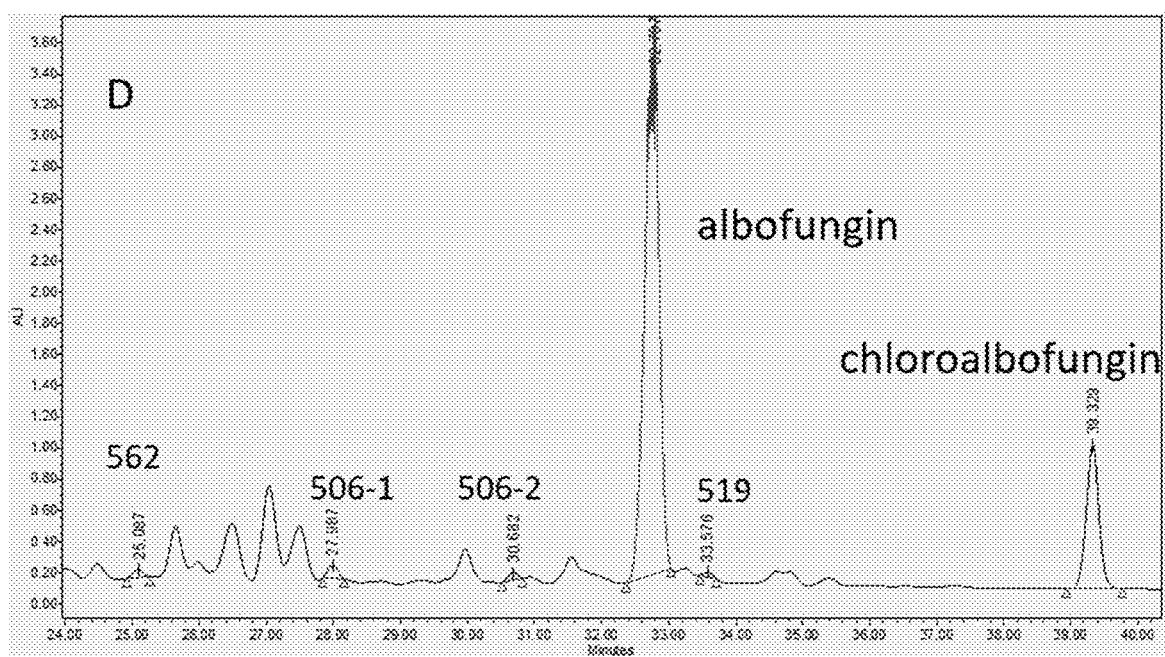

SEQ ID NO: 1: human telomeric variant, htel21_T18
SEQ ID NO: 2: HIV-1 LTR II G4
SEQ ID NO: 3: HIV-1 LTR III G4
SEQ ID NO: 4: HIV-1 LTR IV G4

DETAILED DISCLOSURE OF THE INVENTION

Selected Definitions

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed.

In the present disclosure, ranges are stated in shorthand, to avoid having to set out at length and describe each and every value within the range. Any appropriate value within the range can be selected, where appropriate, as the upper value, lower value, or the terminus of the range. For example, a range of 1-10 represents the terminal values of 1 and 10, as well as the intermediate values of 2, 3, 4, 5, 6, 7, 8, 9, and all intermediate ranges encompassed within 1-10, such as 2-5, 2-8, and 7-10. Also, when ranges are used herein, combinations and sub-combinations of ranges (e.g., subranges within the disclosed range) and specific embodiments therein are intended to be explicitly included.

In certain embodiments of the invention a subject is a mammal. Non-limiting examples of a mammal treatable according to the methods of the current invention include a human. Additional examples of mammals treatable with the methods of the current invention are well known to a person of ordinary skill in the art and such embodiments are within the purview of the current invention.

For the purposes of this invention the terms "treatment, treating, treat" or equivalents of these terms refer to healing, alleviating, relieving, altering, remedying, ameliorating, improving, or affecting the condition or the symptoms of a subject suffering with a disease, for example, a human immunodeficiency virus (HIV) and/or human immunodeficiency virus infection and Acquired Immunodeficiency Syndrome (HIV/AIDS). When provided therapeutically, the compound can be provided at (or after) a viral infection. The therapeutic administration of the substance serves to attenuate any actual symptom and/or inhibit viral replication.

By "therapeutically effective dose," "therapeutically effective amount", or "effective amount" is intended to be an amount of a compounds of the subject invention disclosed herein that, when administered to a subject, decreases the number of viruses or severity of symptoms, reduces any increase in symptoms, or improve the clinical course of the disease as compared to untreated subjects. "Positive therapeutic response" refers to, for example, improving the condition of HIV.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Generally, the dosage of the compounds of the subject invention will vary depending upon such factors as the patient's age, weight, height, sex, general medical condition and previous medical history.

In some embodiments of the invention, the method comprises administration of multiple doses of the compounds of the subject invention. The method may comprise administration of 1, 2, 3, 4, 5, 6, 7, 8, 9, 10, 15, 20, 25, 30, 35, 40, or more therapeutically effective doses of a composition comprising the compounds of the subject invention as described herein. In some embodiments, doses are administered over the course of 1 day, 2 days, 3 days, 4 days, 5 days, 6 days, 7 days, 10 days, 14 days, 21 days, 30 days, 2 months, 6 months, 1 year, years, 5 years, 10 years, 15 years, 20 years, 25 years, or longer. The frequency and duration of administration of multiple doses of the compositions is such as to reduce HIV viral load in an infected subject. Moreover, treatment of a subject with a therapeutically effective amount of the compounds of the invention can include a single treatment or can include a series of treatments. It will also be appreciated that the effective dosage of a compound used for treatment may increase or decrease over the course of a particular treatment. Changes in dosage may result and become apparent from the results of diagnostic assays for detecting HIV known in the art. In some embodiments of the invention, the method comprises administration of the compounds several time per day, including but not limiting to 2 times per day, 3 times per day, and 4 times per day.

Compounds

In preferred embodiments, the compositions and methods according to the subject invention utilize isolated albofungin and derivatives thereof, including, for example chloroalbofungin, 477-albo, 492-albo, 505-albo, 506-1-albo, 506-2-albo, 519-albo, and 562-albo, and/or bacterial culture extracts containing albofungin and derivatives thereof. Albofungin and derivatives thereof, including, for example chloroalbofungin, 477-albo, 492-albo, 505-albo, 506-1-albo, 506-2-albo, 519-albo, and 562-albo may be in a purified form or in a mixture of bacterial growth products, including crude extracts. Compounds albofungin and derivatives thereof may be added to compositions at concentrations of about 0.0001 to about 5% by weight (wt %), preferably about 0.01 to about 5 wt %, and more preferably about 0.1 to about 1 wt %. In another embodiment, purified compounds albofungin and derivatives thereof may be in combination with an acceptable carrier, in that compounds albofungin and derivatives thereof may be presented at concentrations of about 0.0001 to about 5% (v/v), preferably, about 0.01 to about 5% (v/v), more preferably, about 0.1 to about 1% (v/v).

The following are chemical formulas of albofungin (Formula (I)) and derivatives thereof, including chloroalbofungin (Formula (II)), 506-1-albo (Formula (III)), 506-2-albo (Formula (IV)), 519-albo (Formula (V)), 562-albo (Formula (VI)) 477-albo (Formula (VII)), 492-albo (Formula (VIII)), and 505-albo (Formula (IX)):

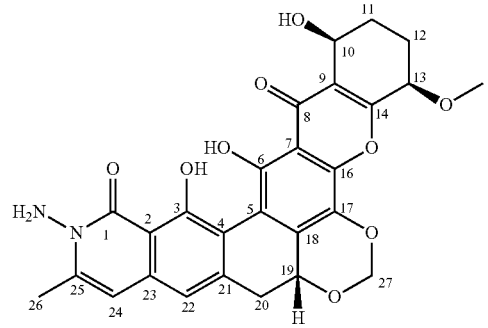

Albofungin

Formula (I)

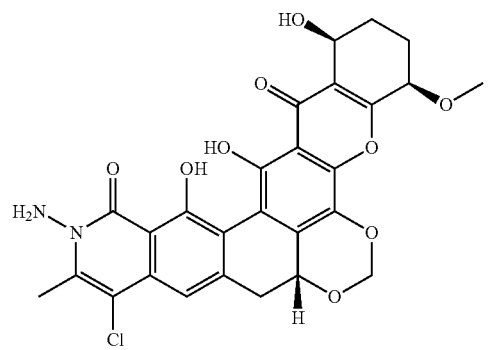

Chloroalbofungin

Formula (II)

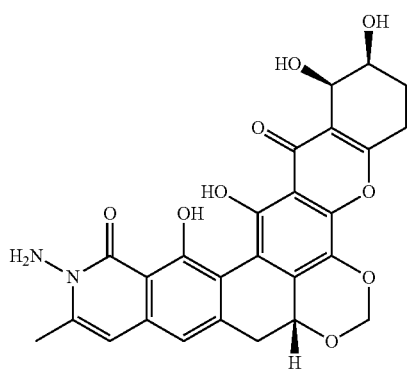

506-1-Albo

Formula (III)

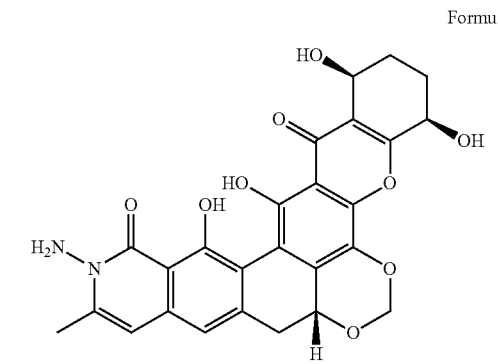

506-2-Albo

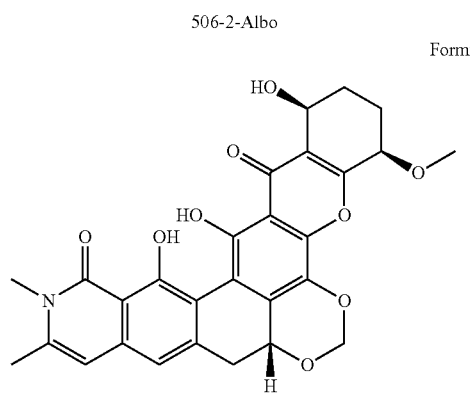

519-Albo

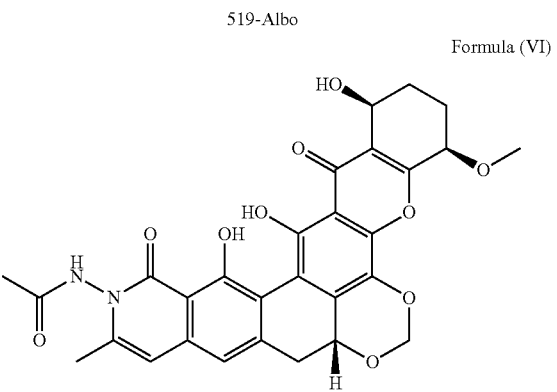

562-Albo

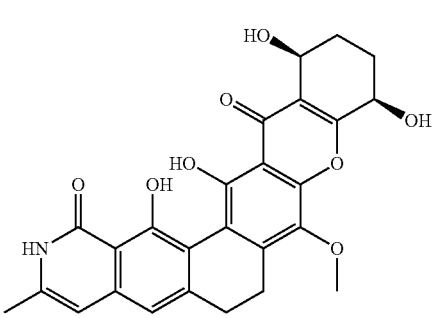

477-Albo

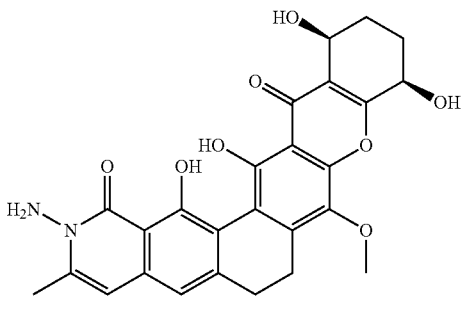

492-Albo

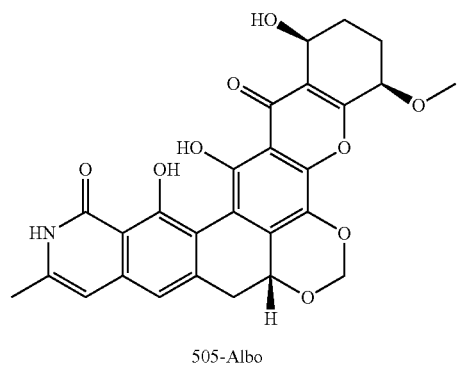

505-Albo

The microorganisms utilized according to the subject invention may be natural, or genetically modified microorganisms, specifically microorganisms that can synthesize the compounds of the subject invention. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain embodiments, the microorganisms are any bacteria that produce compounds albofungin and derivatives thereof, including, for example, chloroalbofungin, 477-albo, 492-albo, 505-albo, 506-1-albo, 506-2-albo, 519-albo, and 562-albo. Albofungin and derivatives thereof, including, for example chloroalbofungin, 477-albo, 492-albo, 505-albo, 506-1-albo, 506-2-albo, 519-albo, and 562-albo and/or associated bacteria culture extracts can be produced by bacteria, including *Streptomyces* spp. In preferred embodiments, albofungin and derivatives thereof, including, for example chloroalbofungin, 477-albo, 492-albo, 505-albo, 506-1-albo, 506-2-albo, 519-albo, and 562-albo are produced by *Streptomyces chrestomyceticus* BCC 24770.

In one embodiment, the method for cultivation of microorganisms is carried out at about 5° C. to about 100° C., about 15° C. to about 60° C., about 20° C. to about 37° C., preferably, about 20° C. to about 30° C., or, more preferably, about 23° C. to about 30° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. In certain embodiments, the bacteria can undergo fermentation, said fermentation comprising contacting bacterial cells to GYM medium (4 g of yeast extract, 10 g of malt extract, and 4 g of D-glucose per liter of distilled water) or SPY media (10 g/L of starch, 2 g/L of peptone, 4 g/L of yeast extract and 20 g/L of sea salt) and, optionally, about 20 to about 100 or about 20 to about 30 glass beads (3 mm in diameter) at about 20° C. to 37° C., preferably about 23° C. to about 30° C., for 7 to about 14 days, preferably about 7 to about 14 days, or about 7 to about 10 days or about 10 days, with an agitation of 160 to about 200 rpm or about 180 rpm.

In one embodiment, the compositions of the subject invention comprise a bacterial culture produced according to the subject methods.

The microbial growth by-product produced by microorganisms of interest may be retained in the microorganisms or secreted into the liquid medium. In another embodiment, the method for producing microbial growth by-product may further comprise steps of concentrating and purifying the microbial growth byproduct of interest. In a further embodiment, the liquid medium may contain compounds that stabilize the activity of microbial growth byproduct.

Preparation of Albofungin, Chloroalbofungin, 477-Albo, 492-Albo, 505-Albo, 506-1-Albo, 506-2-Albo, 519-Albo, and 562-Albo and Compositions Thereof One albofungin, chloroalbofungin, 477-albo, 492-albo, 505-albo, 506-1-albo, 506-2-albo, 519-albo, and/or 562-albo-based product of the subject invention is simply the bacterial growth broth containing the bacteria and/or the albofungin, chloroalbofungin, 477-albo, 492-albo, 505-albo, 506-1-albo, 506-2-albo, 519-albo, and/or 562-albo produced by the bacteria and/or any residual nutrients. The product of the bacterial growth may be used directly without extraction or purification. If desired, extraction and purification can be easily achieved using standard extraction and/or purification methods or techniques.

In preferred embodiments, albofungin, chloroalbofungin, 477-albo, 492-albo, 505-albo, 506-1-albo, 506-2-albo, 519-albo, and/or 562-albo can be extracted from the bacteria using ethyl acetate to obtain a crude extract. The crude extract can be separated by reversed-phase C18 column chromatography and eluted with 20, 40, 60, 80, and 100% acetonitrile to obtain different fractions. Compounds can be obtained in the 60% and 80% eluates monitored at a UV wavelength of 210 nm and can be further purified by semi-preparative HPLC. Compounds can be collected, freeze-dried, and dissolved in dimethyl sulfoxide-$d_6$ (DMSO-$d_6$) for further biological assessments.

Upon harvesting the albofungin, chloroalbofungin, 477-albo, 492-albo, 505-albo, 506-1-albo, 506-2-albo, 519-albo, and/or 562-albo compositions from the growth vessels, further components can be added as the harvested product is placed into containers and/or piped (or otherwise transported for use). The additives can be, for example, dyes, pigments, pH adjusting agents, buffers, salts, adhesion-promoting compounds, solvents (e.g., isopropyl alcohol, ethanol), biocides, and other ingredients specific for an intended use.

In certain embodiments, the albofungin, chloroalbofungin, 477-albo, 492-albo, 505-albo, 506-1-albo, 506-2-albo, 519-albo, and/or 562-albo compositions can be added to existing compositions that are traditionally used as therapeutics.

In one embodiment, the subject compositions are formulated as an orally-consumable product, such as, for example a food item, capsule, pill, or drinkable liquid. An orally deliverable pharmaceutical is any physiologically active substance delivered via initial absorption in the gastrointestinal tract or into the mucus membranes of the mouth. The topic compositions can also be formulated as a solution that can be administered via, for example, injection, which includes intravenously, intraperitoneally, intramuscularly, intrathecally, intracerebroventricularly or subcutaneously. In other embodiments, the subject compositions are formulated to be administered via the skin through a patch or directly onto the skin for local or systemic effects. The compositions can be administered sublingually, buccally, rectally, or vaginally. Furthermore, the compositions can be sprayed into the nose for absorption through the nasal membrane, nebulized, inhaled via the mouth or nose, or administered in the eye or ear.

Orally consumable products according to the invention are any preparations or compositions suitable for consumption, for nutrition, for oral hygiene, or for pleasure, and are products intended to be introduced into the human or animal oral cavity, to remain there for a certain period of time, and then either be swallowed (e.g., food ready for consumption or pills) or to be removed from the oral cavity again (e.g., chewing gums or products of oral hygiene or medical mouth washes). While an orally-deliverable pharmaceutical can be formulated into an orally consumable product, and an orally consumable product can comprise an orally deliverable pharmaceutical, the two terms are not meant to be used interchangeably herein.

Orally consumable products include all substances or products intended to be ingested by humans or animals in a processed, semi-processed, or unprocessed state. This also includes substances that are added to orally consumable products (particularly food and pharmaceutical products) during their production, treatment, or processing and intended to be introduced into the human or animal oral cavity.

Orally consumable products can also include substances intended to be swallowed by humans or animals and then digested in an unmodified, prepared, or processed state; the orally consumable products according to the invention therefore also include casings, coatings, or other encapsulations that are intended to be swallowed together with the product or for which swallowing is to be anticipated.

In one embodiment, the orally consumable product is a capsule, pill, syrup, emulsion, or liquid suspension containing a desired orally deliverable substance. In one embodiment, the orally consumable product can comprise an orally deliverable substance in powder form, which can be mixed with water or another liquid to produce a drinkable orally-consumable product.

In some embodiments, the orally-consumable product according to the invention can comprise one or more formulations intended for nutrition or pleasure. These particularly include baking products (e.g., bread, dry biscuits, cake, and other pastries), sweets (e.g., chocolates, chocolate bar products, other bar products, fruit gum, coated tablets, hard caramels, toffees and caramels, and chewing gum), alcoholic or non-alcoholic beverages (e.g., cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, and fruit or vegetable juice preparations), instant beverages (e.g., instant cocoa beverages, instant tea beverages, and instant coffee beverages), meat products (e.g., ham, fresh or raw sausage preparations, and seasoned or marinated fresh meat or salted meat products), eggs or egg products (e.g., dried whole egg, egg white, and egg yolk), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, whey, butter, buttermilk, and partly or wholly hydrolyzed products containing milk proteins), products from soy protein or other soy bean fractions (e.g., soy milk and products prepared thereof, beverages containing isolated or enzymatically treated soy protein, soy flour containing beverages, preparations containing soy lecithin, fermented products such as tofu or tempeh products prepared thereof and mixtures with fruit preparations and, optionally, flavoring substances), fruit preparations (e.g., jams, fruit ice cream, fruit sauces, and fruit fillings), vegetable preparations (e.g., ketchup, sauces, dried vegetables, deep-freeze vegetables, pre-cooked vegetables, and boiled vegetables), snack articles (e.g., baked or fried potato chips (crisps) or potato dough products and extrudates on the basis of maize or peanuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening or whitening beverages or other food). The present compositions may also serve as semi-finished products for the production of other compositions intended for nutrition or pleasure.

The subject composition can further comprise one or more pharmaceutically acceptable carriers, and/or excipients, and can be formulated into preparations, for example, solid, semi-solid, liquid, or gaseous forms, such as tablets, capsules, powders, granules, ointments, solutions, suppositories, injections, inhalants, and aerosols.

The term "pharmaceutically acceptable" as used herein means compatible with the other ingredients of a pharmaceutical composition and not deleterious to the recipient thereof.

Carriers and/or excipients according the subject invention can include any and all solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol) and the like. The use of carriers and/or excipients in the field of drugs and supplements is well known. Except for any conventional media or agent that is incompatible with the target health-promoting substance or with the composition, carrier or excipient use in the subject compositions may be contemplated.

In one embodiment, the compositions of the subject invention can be made into aerosol formulations so that, for example, it can be nebulized or inhaled. Suitable pharmaceutical formulations for administration in the form of aerosols or sprays are, for example, powders, particles, solutions, suspensions or emulsions. Formulations for oral or nasal aerosol or inhalation administration may also be formulated with carriers, including, for example, saline, polyethylene glycol or glycols, DPPC, methylcellulose, or in mixture with powdered dispersing agents or fluorocarbons. Aerosol formulations can be placed into pressurized propellants, such as dichlorodifluoromethane, propane, nitrogen, fluorocarbons, and/or other solubilizing or dispersing agents known in the art. Illustratively, delivery may be by use of a single-use delivery device, a mist nebulizer, a breath-activated powder inhaler, an aerosol metered-dose inhaler (MDI), or any other of the numerous nebulizer delivery devices available in the art. Additionally, mist tents or direct administration through endotracheal tubes may also be used.

In one embodiment, the compositions of the subject invention can be formulated for administration via injection, for example, as a solution or suspension. The solution or suspension can comprise suitable non-toxic, parenterally-acceptable diluents or solvents, such as mannitol, 1,3-butanediol, water, Ringer's solution, or isotonic sodium chloride solution, or suitable dispersing or wetting and suspending agents, such as sterile, non-irritant, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

In one embodiment, the compositions of the subject invention can be formulated for administration via topical application onto the skin, for example, as topical compositions, which include rinse, spray, or drop, lotion, gel, ointment, cream, foam, powder, solid, sponge, tape, vapor, paste, tincture, or using a transdermal patch. Suitable formulations of topical applications can comprise in addition to any of the pharmaceutically active carriers, for example, emollients such as carnauba wax, cetyl alcohol, cetyl ester wax, emulsifying wax, hydrous lanolin, lanolin, lanolin alcohols, microcrystalline wax, paraffin, petrolatum, polyethylene glycol, stearic acid, stearyl alcohol, white beeswax, or yellow beeswax. Additionally, the compositions may contain humectants such as glycerin, propylene glycol, polyethylene glycol, sorbitol solution, and 1,2,6 hexanetriol or permeation enhancers such as ethanol, isopropyl alcohol, or oleic acid.

Methods of Using Compounds of the Subject Invention

In certain embodiments, albofungin and derivatives thereof, including, for example chloroalbofungin, 477-albo, 492-albo, 505-albo, 506-1-albo, 506-2-albo, 519-albo, and 562-albo, can be administered to a subject. In certain embodiments, albofungin, chloroalbofungin, 477-albo, 492-albo, 505-albo, 506-1-albo, 506-2-albo, 519-albo, and/or 562-albo can bind to DNA G-quadruplex (G4) and can inhibit viral replication, specifically HIV.

In certain embodiments, albofungin, chloroalbofungin, 477-albo, 492-albo, 505-albo, 506-1-albo, 506-2-albo, 519-albo, and 562-albo, preferably albofungin, 506-1-albo, 506-2-albo, 519-albo, and 562-albo can physically interact with HIV-1 long terminal repeat (LTR) III G-quadruplex (G4). In certain embodiments, albofungin and derivatives thereof, can bind with. In certain embodiments, albofungin and derivatives thereof, including, for example, chloroalbofungin, 477-albo, 492-albo, 505-albo, 506-1-albo, 506-2-albo, 519-albo, and 562-albo, exhibit a stronger binding affinity to LTR III G4 (GG-GAGGCGTGGCCTGGGCGGGACTGGGG (SEQ ID NO: 3)) than to HIV-1 LTR II G4 (GGGGACTTTCCAGG-GAGGCGTGGCCTGGGCGGG (SEQ ID NO: 2)), HIV-1 LTR IV G4 (GGGCGGGACTGGGGAGTGG (SEQ ID NO: 4)), human telomeric variant, htel21_T18 (d[(GGGTTA)$_2$ GGGTTTGGG] (SEQ ID NO: 1), or RNA binding protein, hnRNP A2. Therefore, albofungin and derivatives thereof specifically recognize the HIV-1 LTR III G4 structure.

In certain embodiments, the compounds of the subject invention can contact one or more HIV virions and/or HIV-infected cells. In certain embodiments, the binding of albofungin, chloroalbofungin, 477-albo, 492-albo, 505-albo, 506-1-albo, 506-2-albo, 519-albo, and 562-albo to HIV-1 LTR III, HIV-1 LTR II, or HIV-1 LTR IV can stabilize the G4. Stabilized G4s can reduce viral titer in latent HIV-1 infected cells (20, 21, 22); therefore, G4s can act repressors to regulate viral transcription.

Materials and Methods

Strains

The strain *S. chrestomyceticus* BCC 24770 was purchased from Thailand Bioresource Research Center.

Fermentation, Extraction, and Isolation

*S. chrestomyceticus* BCC 24770 was cultured in two 125-ml Erlenmeyer flasks containing 50 ml of the GYM medium (4 g of yeast extract, 10 g of malt extract, and 4 g of D-glucose per liter of distilled water) and 20-30 glass beads (3 mm in diameter) at about 30° C. and with an agitation of 180 rpm for about three days. Then, 1% of the seed broth was transferred into ten Erlenmeyer flasks containing 1 L of the GYM media and around 100 glass beads for fermentation at about 30° C. with an agitation of about 180 rpm for about ten days. The bacterial culture broth was extracted with an equal volume of ethyl acetate three times to obtain the crude extract. The crude extract was separated by reversed-phase C18 column chromatography and eluted with 20, 40, 60, 80, and 100% acetonitrile to obtain different fractions. Albofungin and its derivatives were obtained in the 60% to 80% eluates and further purified by preparative HPLC (Waters 2695 Separations Module; Milford, USA), eluted with an isocratic mobile phase at a flow rate of 9 ml/min. (Solution A: acetonitrile with 0.5‰ trifluoroacetic acid (TFA); solution B: Milli-Q water with 0.5‰ TFA. Acetonitrile/water ratio was 50%.) The eluate was monitored at a UV wavelength of 210 nm (Waters 2998 Photodiode Array Detector). Compounds were collected, freeze-drying, and dissolved in dimethyl sulfoxide-d$_6$ (DMSO-d$_6$) for both NMR tests and titrations. Phenomenex Luna 5 μm C18(2) 100A, LC Column 250×21.2 mm was used when doing preparative HPLC.

Structural Elucidation $^1$H and $^{13}$C NMR spectra were performed on 500 MHz and 800 MHz Varian spectrometers. Standard 2D NMR experiments, including NOESY, HSQC, HMBC, and COSY, were collected at 25° C. $^1$H and $^{13}$C NMR data of novel derivatives were listed in the following Table 1 and 2. MS data were recorded from a high-resolution Mass Spectrometer (Bruker Daltonics). Optical rotations were determined using a Jasco P-2000 Polarimeter. Circular dichroism spectra were measured using Chirascan Circular Dichroism Spectrometer.

TABLE 1

$^1$H and $^{13}$C NMR Data for 506-1-albo and 506-2 in DMSO-d$_6$

| position | 506-1 albo δ$_C$, type | δ$_H$, mult. (J in Hz) | 506-2 albo δ$_C$, type | δ$_H$, mult. (J in Hz) |
|---|---|---|---|---|
| 1 | 163.4, C | | 163.3, C | |
| 2 | 109.2, C | | 109.2, C | |
| 3 | 156.8, C | | 156.8, C | |
| 4 | 112.9, C | | 112.9, C | |
| 5 | 111.5, C | | 111.4, C | |
| 6 | 149.7, C | | 149.7, C | |
| 7 | 109.7, C | | 109.8, C | |
| 8 | 182.4, C | | 182.3, C | |
| 9 | 117.3, C | | 119.6, C | |
| 10 | 63.1, CH | 4.61, m | 59.0, CH | 4.82, m |
| 11 | 67.0, CH | 3.86, m | 28.2, CH$_2$ | a 1.81, m<br>b 1.71, dd (13.3, 13.3) |
| 12 | 22.4, CH$_2$ | a 2.10, m<br>b 1.84, m | 26.6, CH$_2$ | a 2.07, m<br>b 1.93, m |
| 13 | 22.9, CH$_2$ | a 2.82, m<br>b 2.62, m | 65.5, CH | 4.58, dd (9.6, 6.2) |
| 14 | 167.2, C | | 167.1, C | |
| 16 | 142.6, C | | 142.9, C | |
| 17 | 130.1, C | | 130.3, C | |
| 18 | 129.8, C | | 129.9, C | |
| 19 | 72.2, CH | 4.95, m | 72.1, CH | 4.94, |

TABLE 1-continued

¹H and ¹³C NMR Data for 506-1-albo and 506-2 in DMSO-d₆

| position | 506-1 albo $\delta_C$, type | $\delta_H$, mult. (J in Hz) | 506-2 albo $\delta_C$, type | $\delta_H$, mult. (J in Hz) |
|---|---|---|---|---|
| 20 | 36.0, $CH_2$ | a 3.22, dd (13.9, 4.6)<br>b 2.76, m | 35.9, $CH_2$ | a 3.20, dd (13.7, 4.7)<br>b 2.75, dd (13.7, 13.1) |
| 21 | 140.5, C | | 140.4, C | |
| 22 | 114.7, CH | 7.01, s | 113.8, CH | 6.97, s |
| 23 | 136.3, C | | 136.2, C | |
| 24 | 105.3, C | 6.62, s | 105.3, C | 6.57, s |
| 25 | 141.7, C | | 141.6, C | |
| 26 | 19.0, $CH_3$ | 2.45, s | 18.9, $CH_3$ | 2.44, s |
| 27 | 90.6, $CH_2$ | a 5.39, d (5.9)<br>b 5.60, d (5.9) | 90.5, $CH_2$ | a 5.42, d (5.9)<br>b 5.60, d (5.9) |
| $NH_2$ | | 5.90, s | | ND |
| 3-OH | | 13.57, s | | 13.56, s |
| 6-OH | | 13.12, s | | 13.04, s |
| 10-OH | | 5.30, d (5.3) | | ND |
| 11-OH | | 4.93, m | | |
| 13-OH | | | | ND |

TABLE 2

¹H and ¹³C NMR Data for 519-albo and 562-albo in DMSO-d₆

| position | 519-albo $\delta_C$, type | $\delta_H$, mult. (J in Hz) | 562-albo $\delta_C$, type | $\delta_H$, mult. (J in Hz) |
|---|---|---|---|---|
| 1 | 165.9, C | | 164.4, C | |
| 2 | 109.3, C | | 109.7, C | |
| 3 | 157.6, C | | 157.7, C | |
| 4 | 113.2, C | | 114.0, C | |
| 5 | 111.8, C | | 111.4, C | |
| 6 | 149.6, C | | 149.7, C | |
| 7 | 109.9, C | | 110.0, C | |
| 8 | 182.1, C | | 182.3, C | |
| 9 | 120.4, C | | 120.5, C | |
| 10 | 58.8, CH | 4.83, m | 59.0, CH | 4.81, m |
| 11 | 28.0, $CH_2$ | a 1.73, m<br>b 1.83, m | 28.0, $CH_2$ | a 1.80, m<br>b 1.71, m |
| 12 | 22.8, $CH_2$ | a 2.06, m<br>b 2.08, m | 22.9 $CH_2$ | a 2.05, m<br>b 2.02, m |
| 13 | 74.7, CH | 4.44, dd (8.9, 6.6) | 74.9, CH | 4.42, m |
| 14 | 165.2, C | | 165.5, C | |
| 16 | 142.7, C | | 142.3, C | |
| 17 | 130.3, C | | 130.5, C | |
| 18 | 130.1, C | | 130.3, C | |
| 19 | 72.1, CH | 4.96, dd (13.1, 4.7) | 72.2, CH | 4.95, dd (13.1, 4.8) |
| 20 | 35.9, $CH_2$ | a 3.22, dd (13.9, 4.7)<br>b 2.75, t (13.4) | 35.9, $CH_2$ | a 3.23, dt (14.0, 4.3)<br>b 2.76, q (14.1) |
| 21 | 140.9, C | | 142.0, C | |
| 22 | 113.6, CH | 6.98, s | 114.7, CH | 7.03, s |
| 23 | 137.1, C | | 137.3, C | |
| 24 | 106.5, C | 6.62, s | 105.8, C | 6.61, s |
| 25 | 141.3, C | | 143.1, C | |
| 26 | 20.1, $CH_3$ | 2.45, s | 18.3, $CH_3$ | 2.21, s |
| 27 | 90.4, $CH_2$ | a 5.61, d (5.9)<br>b 5.42, d (5.9) | 90.8, $CH_2$ | a 5.60,<br>b 5.41 |
| NH | | | | 10.91, s |
| N—$CH_3$ | 30.3, $CH_3$ | 3.54, s | | |
| N—Ac | | | 169.6 | |
| Ac—$CH_3$ | | | 20.5 | 2.10, s |
| 3-OH | | 13.97, s | | 13.17, s |
| 6-OH | | 12.93, s | | 12.94, s |
| 10-OH | | 5.14, d (4.7) | | |
| 13-$CH_3$ | 57.5 | 3.56, s | 58.0 | 3.54, s |

¹H and ¹³C data were recorded at 800 and 200 MHz, respectively.

G4 DNA Sample Preparation

The single DNA nucleotides were purchased from Integrated DNA Technologies (IDT). The DNA sample at 100 µM (single strands) was then re-annealed by heating to 95° C. for 15 min, followed by slow cooling to room temperature overnight in an annealing buffer of 70 mM KCl and 20 mM potassium phosphate (pH 7.0). The final NMR samples contained 0.1 mM DNA RNA in 20 mM potassium phosphate buffer (pH 7.0) and 70 mM KCl.

One-Dimensional 1H-NMR Titration Experiments

To verify whether or not the compounds interact with G4 DNA, we performed NMR titration experiments by running one-dimensional (1D) $^1$H NMR spectra at 25° C. All compounds were dissolved in isotope-labeled $d_6$-DMSO (from Sigma-Aldrich) at about 50 mM concentration, working as stock solutions. To avoid chemical shift changes of G4 DNA resulted from $d_6$-DMSO addition, 10 μL $d_6$-DMSO was added into 500 μL of 0.1 mM G4 DNA solution in the NMR buffer (20 mM potassium phosphate buffer and 70 mM KCl, pH 7.0, 10% $D_2O$) and then a 1D $^1$H-NMR spectrum was recorded as a reference. During NMR titration experiments, each compound was added into G4 DNA solution, the maximal volume of 10 μL of each compound in $d_6$-DMSO solution was thought as a final data point.

Expression and Purification of the RRM Domain of hnRNP A2

The coding sequence of the RRM domain of hnRNP A2 was inserted into the expression vector pET-28a(+) (Novagen). The protein was expressed in *Escherichia coli* BL21 (DE3) at 37° C. for 5 h. Cell lysates were subject to affinity purification with the nickel-nitrilotriacetic acid resin (Qiagen) followed by the cleavage of the hexahistidine tag with the P3C enzyme. The resulting protein was further purified on a Superdex 75 column (GE Healthcare). For the NMR studies, the samples uniformly labeled with $^{15}$N isotopes were expressed and purified as described above, except that the cells were grown in an M9 medium containing [$^{15}$N] ammonium chloride (Cambridge Isotopes) and D-glucose.

NMR Titration of the RRM Domain of hnRNP A2 with Compounds or LTR G4s

The titration experiments were performed by recording a series of 2D $^{15}$N-HSQC spectra on uniformly $^{15}$N-labeled RRM domain (~0.1 mM) in the presence of different amounts of DNA ranging from 0 to 0.5 mM at 25° C. The protein sample and the stock solutions of DNA were all prepared in 20 mM potassium phosphate buffer and 70 mM KCl, pH 7.0, 10% $D_2O$.

All compounds were dissolved in isotope-labeled $d_6$-DMSO (from Sigma-Aldrich) at about 50 mM concentration, working as stock solutions. To avoid chemical shift changes of the protein samples resulted from $d_6$-DMSO addition, 10 μL $d_6$-DMSO was added into 500 μL of 0.1 mM the protein solution in the NMR buffer (20 mM potassium phosphate buffer and 70 mM KCl, pH 7.0, 10% D2O) and then a 2D $^{15}$N-HSQC spectrum was conducted as a reference.

CD Spectroscopy

Circular dichroism (CD) spectra were recorded on Chirascan CD spectrometer at 25° C. from 220 nm to 320 nm under liquid mode; a 1 mm path-length quartz cuvette was used in the test.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—The Purification of Albofungin and its Derivatives

Figure 2:
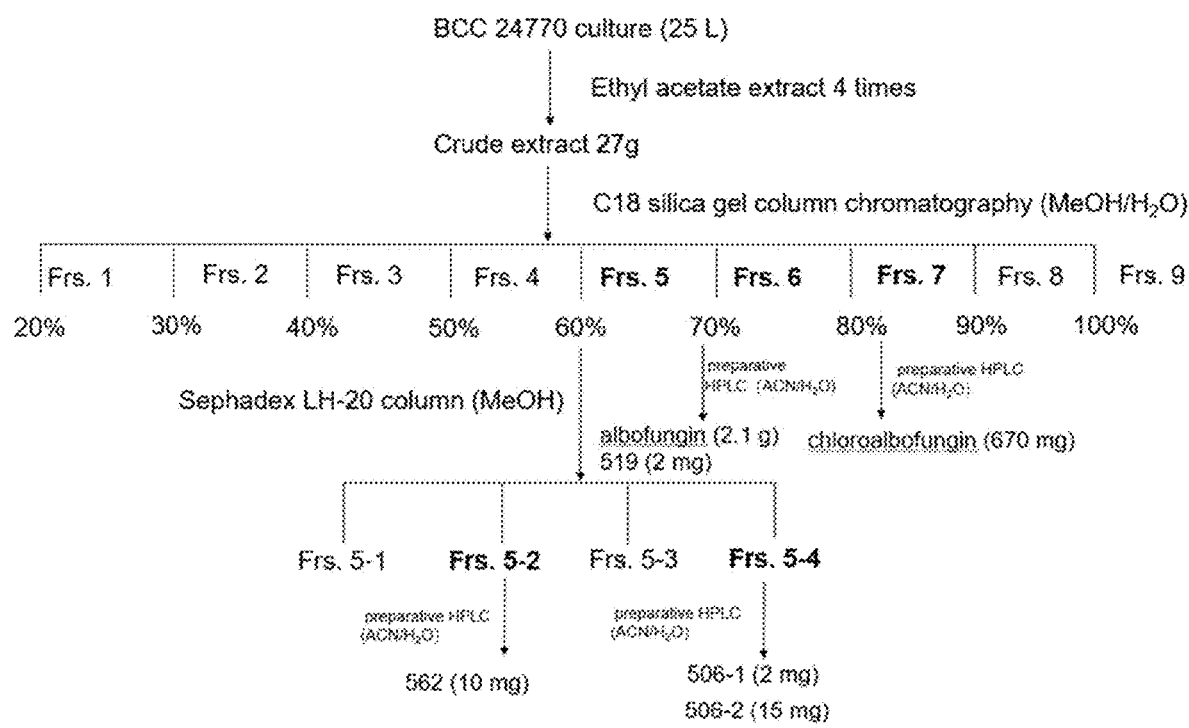
FIG. 2. Isolation of albofungin and its derivatives.

The culture of *Streptomyces chrestomyceticus* BCC 24770 (25 Liters) was extracted with the same volume of ethyl acetate four times and then evaporated under reduced pressure to dry crude extract (27 g). The extracts were loaded to a C18 silica gel column chromatography for fractionation of an increasing gradient of MeOH:$H_2O$ (20%-100%) to give nine fractions. All the fractions were systematically analyzed by HPLC, and fraction 5, fraction 6, and fraction 7 with similar UV patterns were further separated (FIG. 2).

Fraction 5 was loaded to the Sephadex LH-20 column (eluted with MeOH), and the eluates were evaporated to generate four subfractions. Fraction 5-2 was subjected to preparative HPLC (48% acetonitrile 52% $H_2O$ with 0.5‰ trifluoroacetic acid, flow rate 9 mL/min, UV 300 nm detection) to generate compound 4 (10 mg). Fraction 5-4 was subjected to preparative HPLC (Phenomenex Luna 5 μm C18(2) 100A, LC Column 250×21.2 mm, 45% acetonitrile-55% $H_2O$ with 0.5‰ trifluoroacetic acid) to yield compound 1 (2 mg) and compound 2 (15 mg). Fraction 6 was further purified by preparative HPLC with 50% acetonitrile to obtained compound 3 (2 mg) and compound 5 (2.1 g). Fraction 7 was purified by preparative HPLC (60% acetonitrile with 0.5‰ trifluoroacetic acid to yield compound 6 (670 mg).

Example 2—The Structure Elucidation of Albofungin and its Derivatives

Figure 3:
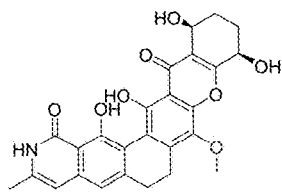
FIG. 3. Structures of albofungin and its derivatives.
Figure 3:
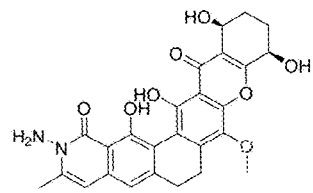
Figure 3:
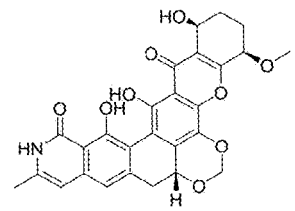
Figure 3:
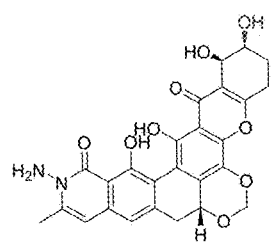
Figure 3:
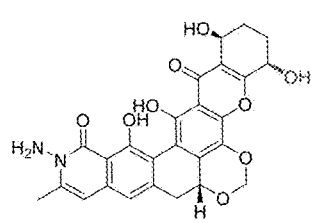
Figure 3:
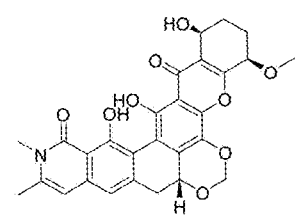
Figure 3:
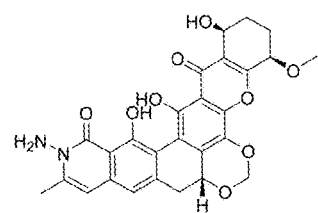
Figure 3:
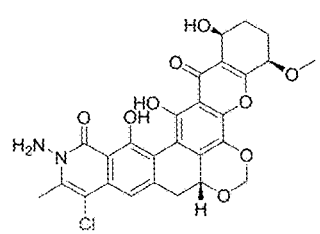
Figure 3:
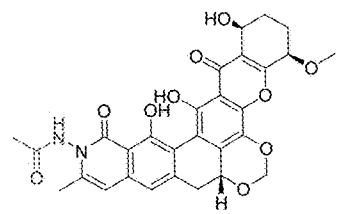

The known antibiotics albofungin and its chlorinated derivative have a very high yield in the crude extracts of *Streptomyces chrestomyceticus* BCC 24770. Their single crystals were obtained, and single-crystal XRD data was collected. (18) Hence their absolute configurations were confirmed. The structures of other novel derivatives were established through comparison with albofungin (FIG. 3, Table 1 and Table 2).

Example 3—Albofungin Specifically Recognizes HIV-1 LTR III G4

Figure 4:
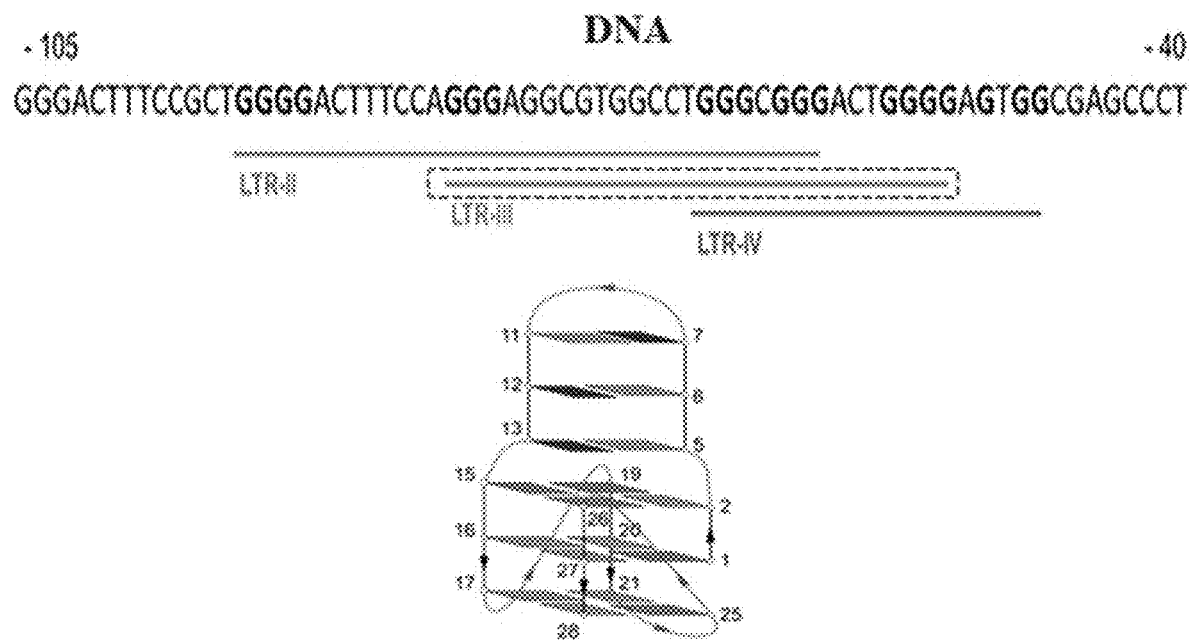
FIG. 4. The sequence of LTR II, LTR III, LTR IV, and the schematic structure of LTR III G4. LTR G-rich sequence in the U3 promoter region of HIV-1 proviral genome and the associated subsequences LTR-II, LTR-III, and LTR-IV, and the known G4 structure formed by LTR-III contains a duplex.
Figure 5:
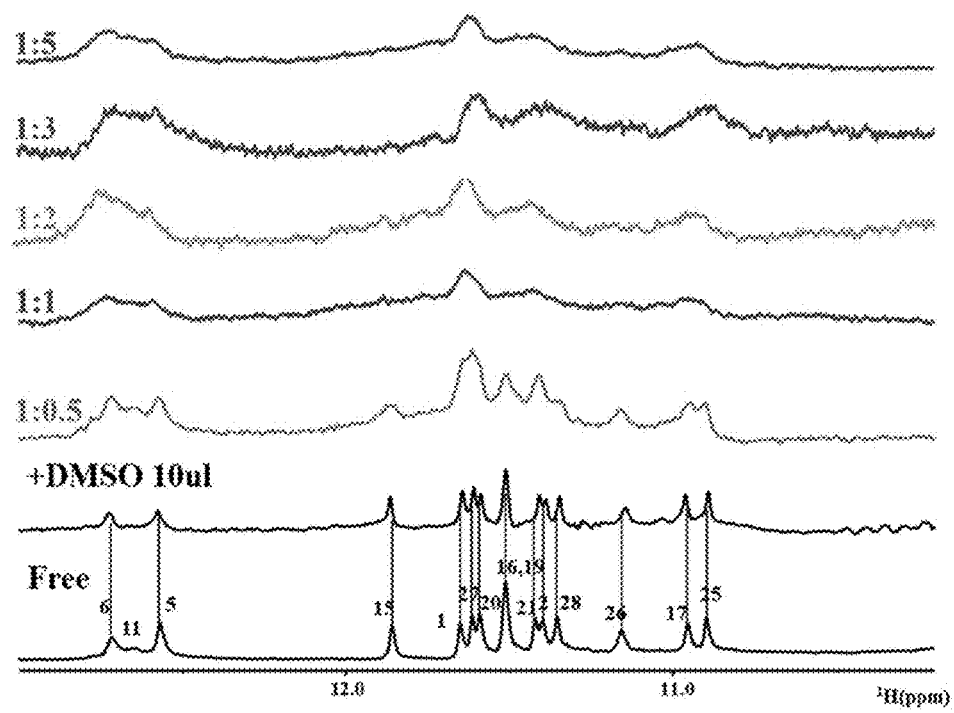
FIG. 5. Titration of albofungin with HIV-1 LTR III G4. The imino region of the 1D $^1$H-NMR spectra of the LTR III G4, and that titrated with albofungin at the ratio of 1:0, 1:0.5, 1:1, 1:2, and 1:5.

Three overlapping and mutually exclusive G4s can form in the LTR G-rich U3 promoter region of the HIV-1 proviral genome, LTR-II, LTR-III, and LTR IV (19) (FIG. 4). Extensive studies show that stabilized G4s could reduce viral titer in latent HIV-1 infected cells (20, 21, 22); in other words, G4s act as repressor to regulate viral transcription. Among the three G4s, LTR III was shown to be the major conformation in vitro (19). Subsequently, we performed NMR titration experiments (23) to screen potential small molecules from our bacterial secondary metabolites library using LTR III G4. According to the 1D $^1$H-NMR spectrum titrated with different concentration ratios of G4: albofungin, significant chemical shift changes in the peaks of G15, G1, G27, G20, G16, G19, G21, G2, G28, G17, and G25 were observed at a concentration ratio of 1:0.5 (FIG. 5). The imino region of the 1D 1H-NMR spectra of the LTR III G4 almost broadened when the ratio was increased from 1:1 to 1:5, indicating a potent interaction between the compound and the LTR III G4.

Example 4—Albofungin Shows Weak/Poor Binding Affinity with Other LTR G4S

Figure 6:
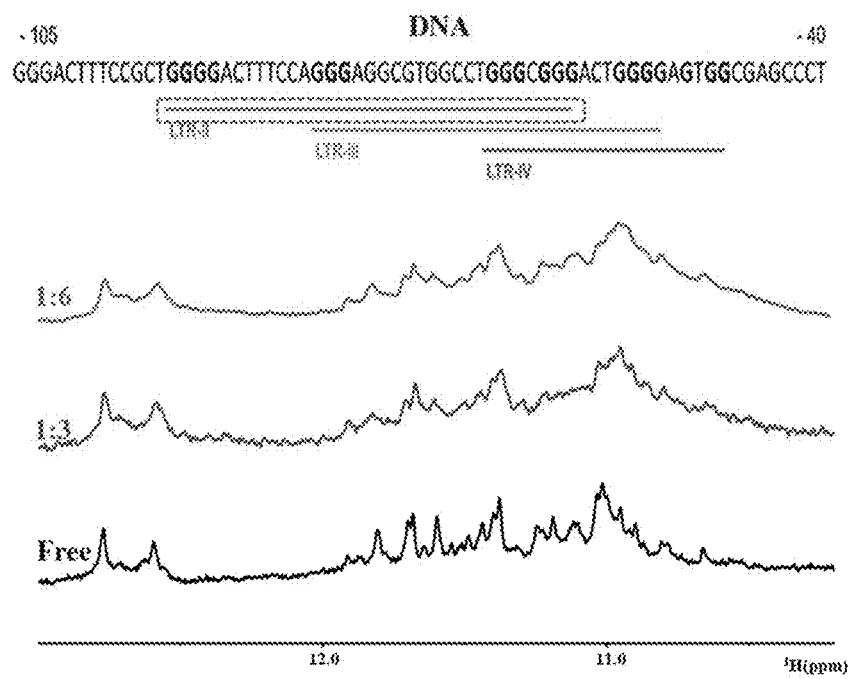
FIG. 6. Titration of albofungin with HIV-1 LTR II G4. The imino region of the 1D $^1$H-NMR spectra of the LTR II G4, and that titrated with albofungin at the ratio of 1:0, 1:3, and 1:6.
Figure 7:
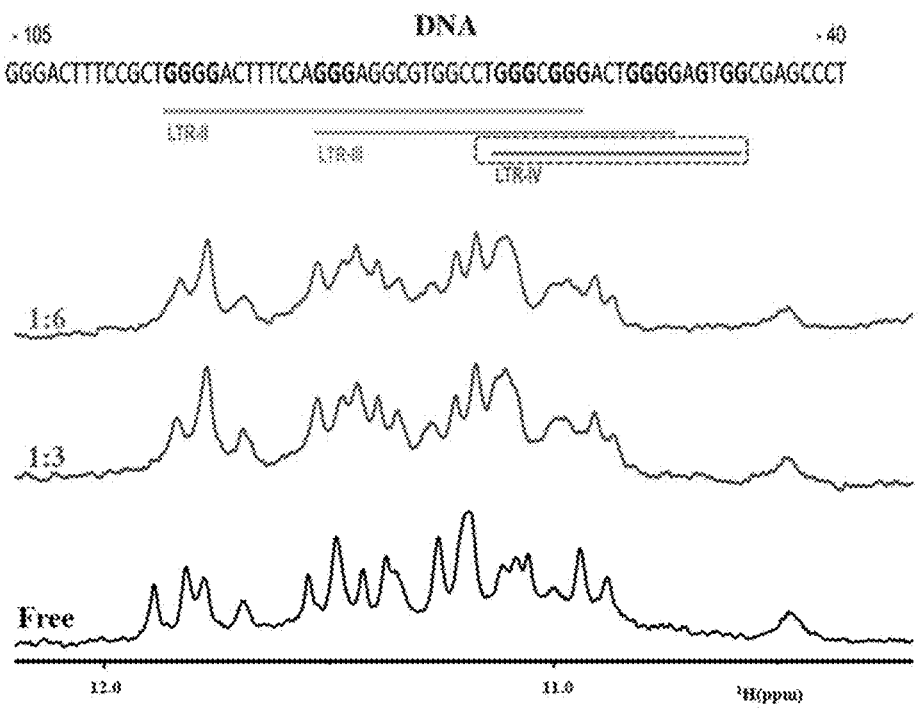
FIG. 7. Titration of albofungin with HIV-1 LTR IV G4. The imino region of the 1D $^1$H-NMR spectra of the LTR IV G4, and that titrated with albofungin at the ratio of 1:0, 1:3, and 1:6.

Since not only LTR III can form noncanonical G4, LTR II and LTR IV can also form mutually exclusive G4 structures (24). To test whether albofungin binds to all types of G4s formed by LTR, we conducted the NMR titration of LTR II (FIG. 6) and LTR IV (FIG. 7) G4s with albofungin at a ratio of 1:0, 1:3, and 1:6, respectively. The 1D $^1$H NMR spectra showed that no significant chemical shift changes were observed even at a concentration ratio of 1:6, further indicating the specific binding of albofungin with LTR III G4.

Example 5—Albofungin does not Bind to Human Telomeric Htel21_T18 G4

Figure 8:
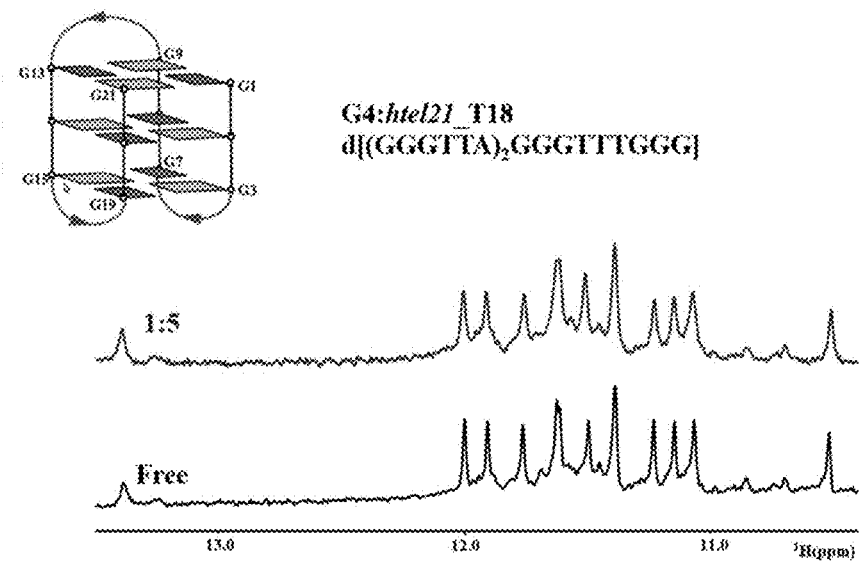
FIG. 8. Titration of albofungin with htel21_T18. The schematic structure of human telomeric htel21_T18 G-quadruplex was shown upon. Below was the imino region of the 1D $^1$H-NMR spectra of human telomeric htel21_T18 d[(GGGTTA)$_2$GGGTTTGGG] (SEQ ID NO: 1) G-quadruplex and that titrated with albofungin at the ratio of 1:5.

The LTR sequence and other G-rich DNA or RNA strands can form polymorphic G4s. For example, a chair-type conformation is adopted by a human telomeric variant, htel21_T18 (d[(GGGTTA)$_2$GGGTTTGGG]) (SEQ ID NO: 1) (25). NMR titration of albofungin with htel21_T18 was performed. Surprisingly, the 1D $^1$H NMR spectra of htel21_T18 titrated with albofungin showed no chemical shift changes at the concentration ratio of 1:5 (FIG. 8).

In other words, albofungin specifically recognizes HIV-1 LTR III G4 structure, indicating a high selectivity as a potential drug lead.

Example 6—Albofungin Inhibits the Binding of Human Ribonucleoprotein A2 (HNRNP A2) with LTR III G4

Figure 9:
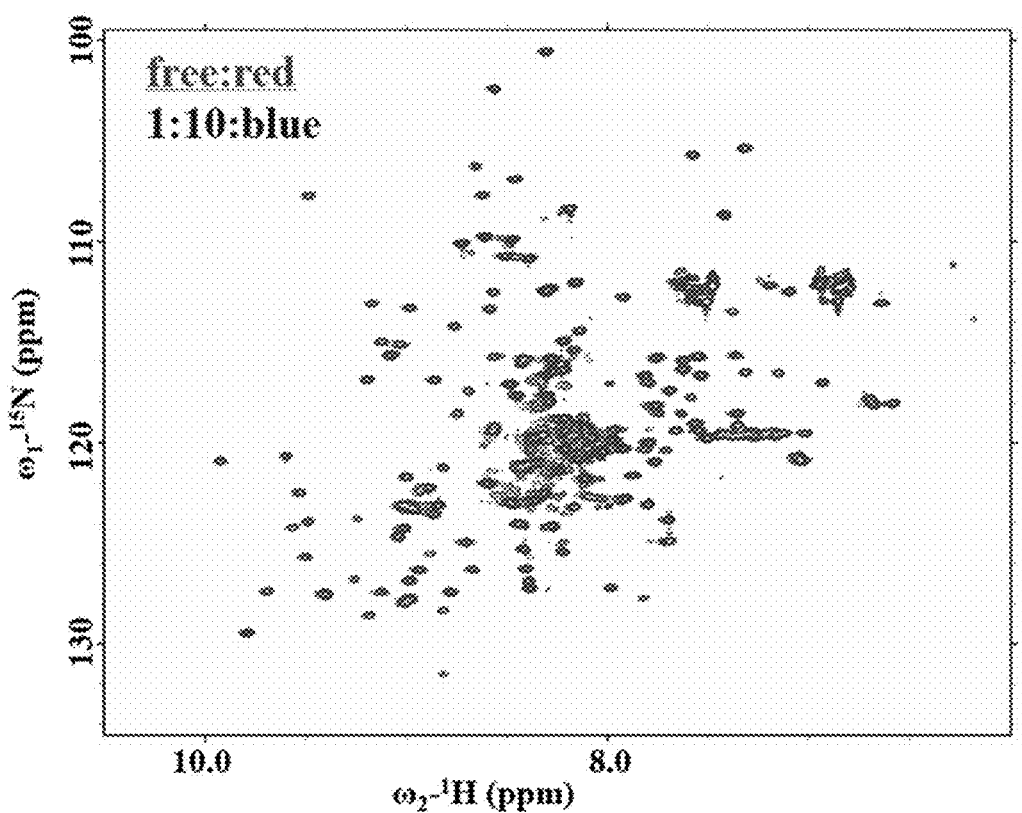
FIG. 9. Titration of hnRNP A2_RRM1,2 with albofungin. The overlayed $^1$H-$^{15}$N HSQC spectra of RRM1,2 domain of hnRNP A2 in free form (red) and titrated with albofungin at 1:10 (blue).
Figure 10:
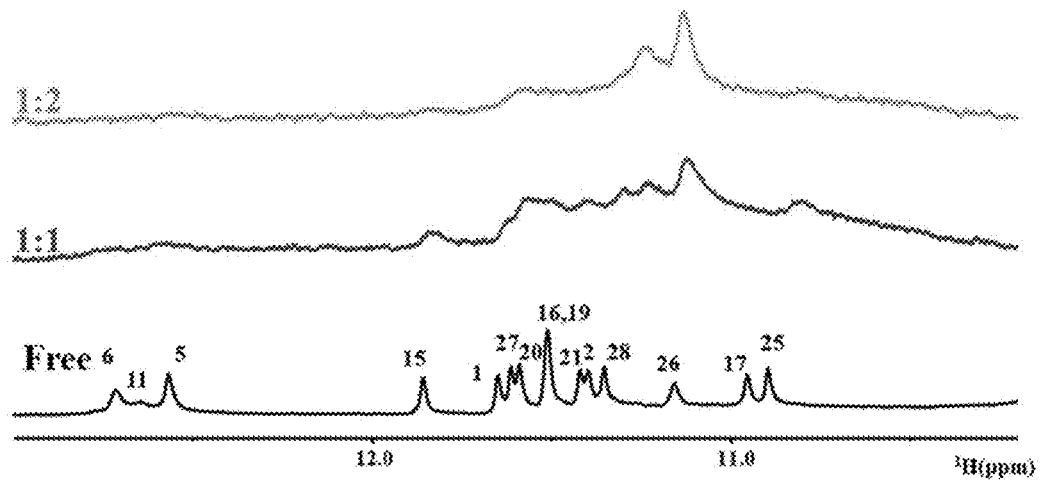
FIG. 10. Titration of HIV-1 LTR III G4 with RRM1,2 domain of hnRNP A2. The imino region of the 1D $^1$H-NMR spectra of the LTR III G4, and that titrated with RRM1,2 domain of hnRNP A2 at the ratio of 1:1 and 1:2.
Figure 11:
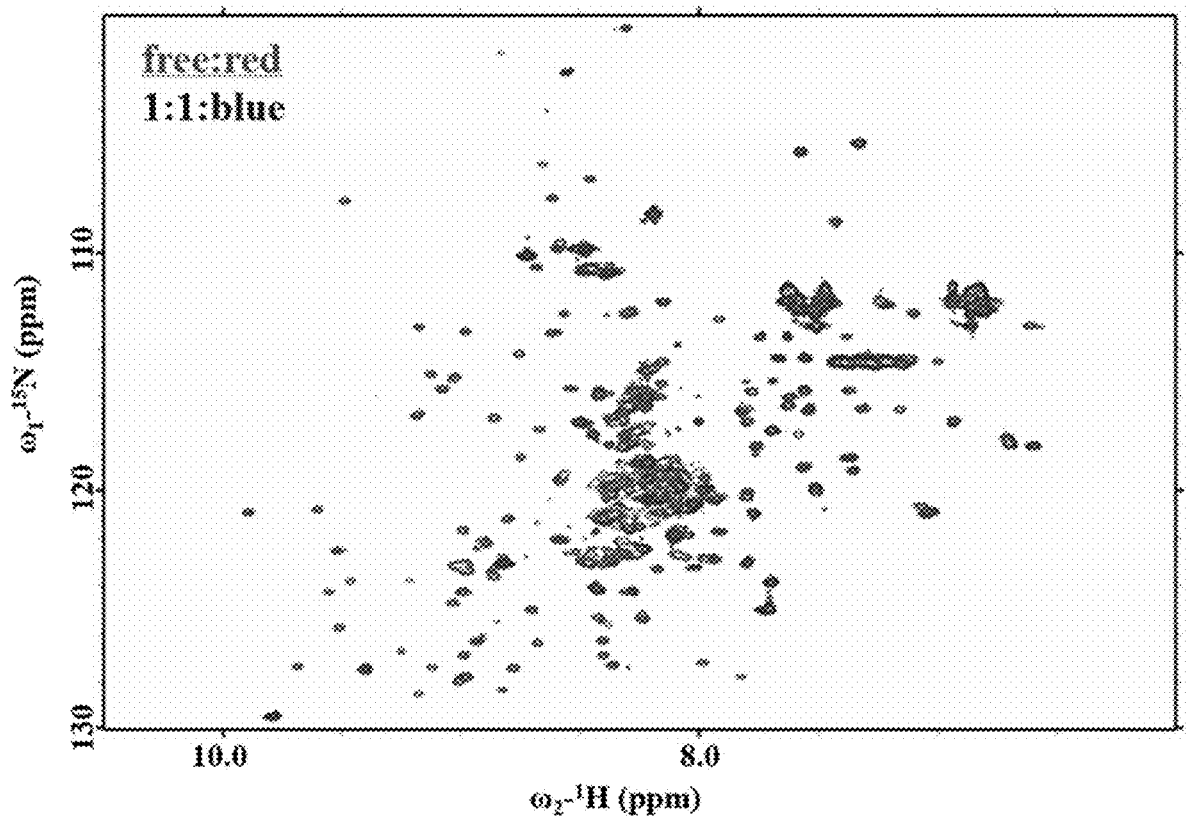
FIG. 11. Titration of hnRNP A2_RRM1,2 with HIV-1 LTR III G4. The overlayed $^1$H-$^{15}$N HSQC spectra of RRM1,2 domain of hnRNP A2 in free form (red) and titrated with LTR III G4 at 1:1 (blue).
Figure 12:
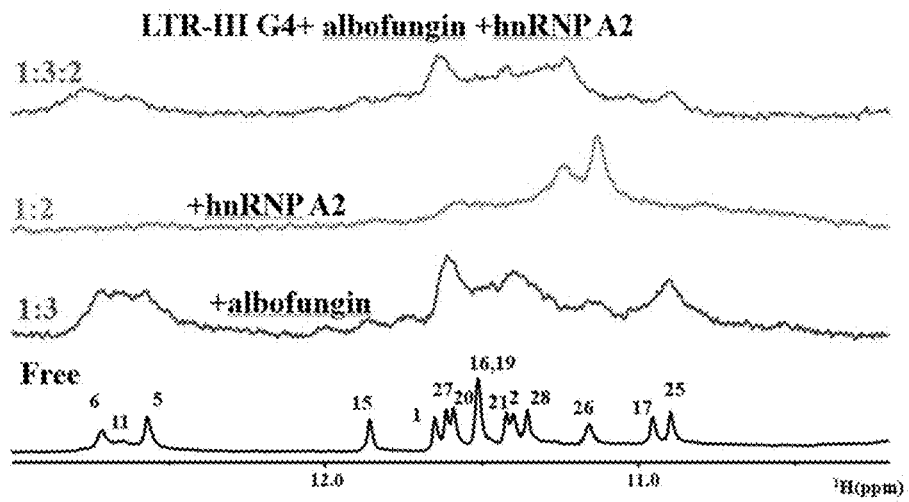
FIG. 12. Titration of HIV-1 LTR III G4 with albofungin and RRM1,2 domain of hnRNP A2. The imino region of the 1D $^1$H-NMR spectra of the LTR III G4, and that titrated with albofungin at the ratio of 1:3 (bottom), with RRM1,2 domain of hnRNP A2 at the ratio of 1:2 (middle), and with albofungin and hnRNP A2 together at the ratio of 1:3:2.

LTR G4 region is under control of two nuclear proteins: nucleolin, which upon binding increases LTR G4 stability and thus silences transcription (26); the human ribonucleoprotein (hnRNP) A2/B1, which can unfold the LTR G4 efficiently and thus enhances HIV-1 transcription (27). To sum up, G4 binding proteins perform like a switch in the determination of G4's conformation to control viral transcription modulation. Therefore, the RRM domain of human ribonucleoprotein (hnRNP A2) was expressed and purified, and the NMR titration of LTR III G4 with the RRM domain of hnRNP A2 was performed. Not surprisingly, significant chemical shift changes in the imino region of the 1D $^1$H-NMR spectrum of LTR III G4 were observed at a concentration ratio of 1:1 (FIG. 10), indicating the strong binding with the RRM domain of hnRNP A2. This is consistent with the observation of chemical shift changes in the $^{15}$N-$^1$H HSQC spectra of the RRM1,2 domain of hnRNP A2 titrated with LTR III G4 (FIG. 11). However, the RRM domain of hnRNP A2 did not bind with albofungin (FIG. 9). Intriguingly, as shown in FIG. 12, when RRM1,2 domain of hnRNP A2 was added into complex of LTR III G4/albofungin (at the concentration ratio of 1:3), no changes in the profile of the imino region were observed in the 1D $^1$H-NMR spectrum, implying that albofungin occupied the binding sites of LTR III G4 that interacting with hnRNP A2 and thus led to disruption of the protein/G4 interactions. Considering albofungin's poor solubility in solution, the real binding activity could be better, making albofungin a promising HIV-1 LTR III G-quadruplex ligand to treat HIV-1 infection. Since poor water solubility will constrain the bioavailability and would be detrimental to quantifying binding affinity, derivatives with better solubility will benefit. Among all the derivatives, a compound with molecular 477 stands out.

Figure 13:
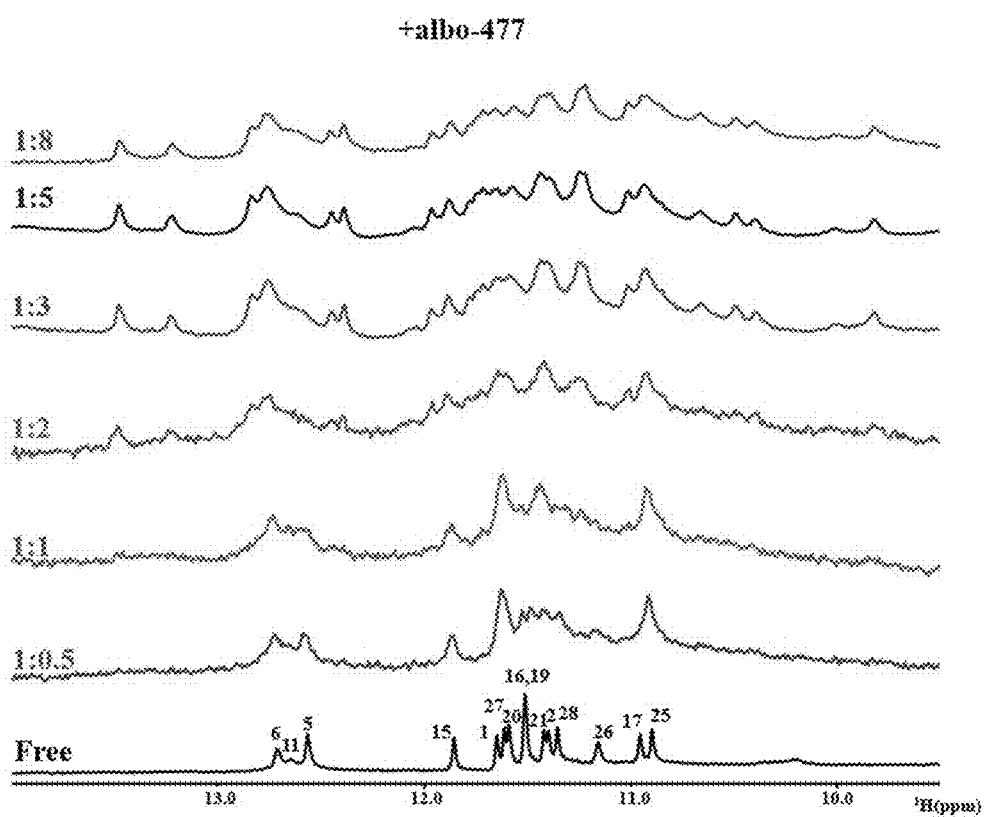
FIG. 13. Titration of 477-albo with HIV-1 LTR III G4. The imino region of the 1D $^1$H-NMR spectra of the LTR III G4, and that titrated with 477-albo at the ratio of 1:0, 1:0.5, 1:1, 1:2, 1:3, 1:5 and 1:8; imino regions' signal has a clear trend of chemical shifts changes when titrating of 477-albo.
Figures 14A, 14B, 14C:
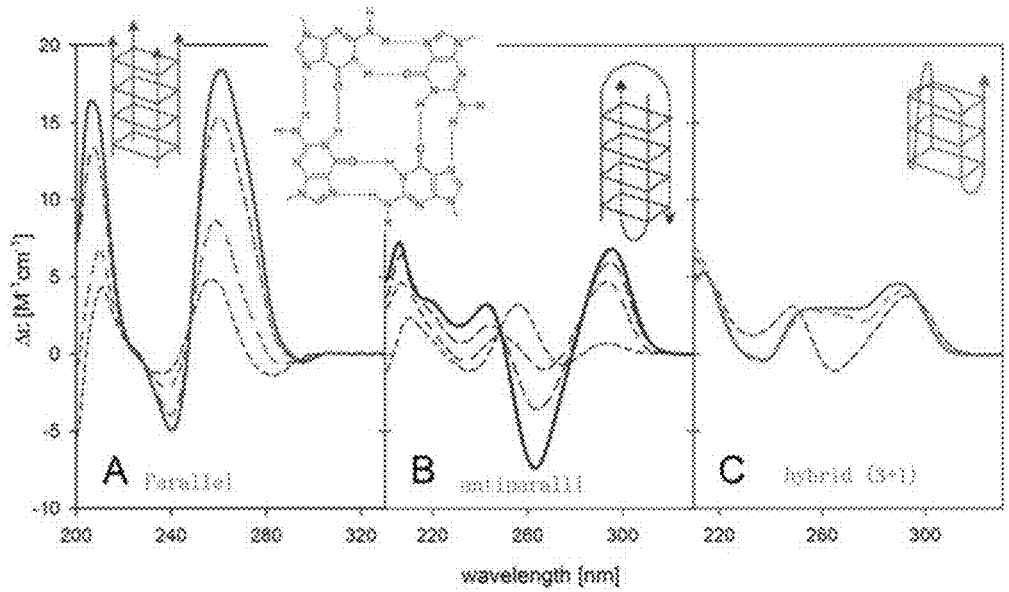
FIGS. 14A-14D. CD spectra of different types of G4s (FIGS. 14A-14C) and LTR-III G4's CD spectra changes when adding 477-albo (FIG. 14D). Different types of G4s have distinct CD spectra.
Figure 14D:
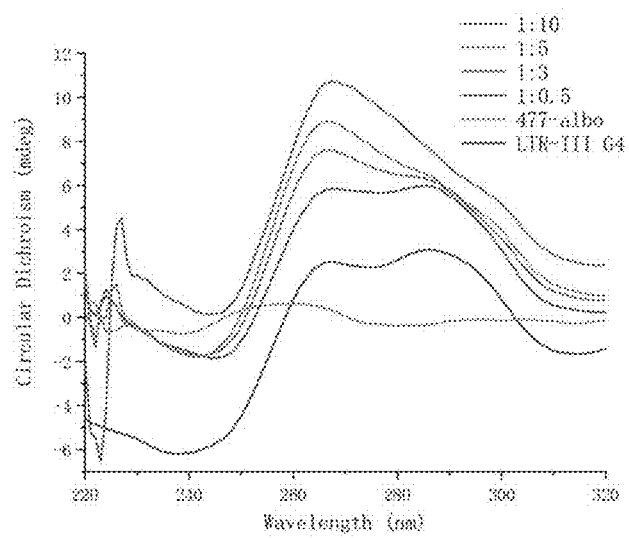

Example 7—477-Albo Changes LTR-III G4's Conformation 477-albo has better solubility in the solvent system, and it will not precipitate at the test concentration; it is also unlike albofungin, which exhibits significant binding affinity under a concentration ratio of 1:0.5, broadening the imino regions' signal, a clear trend of chemical shifts changes can be observed when titrating of 477-albo (FIG. 13). Interestingly, several strange shifts (between 13 to 14 ppm and 9.5 to 10.5 ppm) appear when the concentration ratio increases to 1:3, indicating the conformation change. Except for NMR titration and X-ray diffraction; Circular Dichroic (CD) spectroscopy is another frequently used method for G4 studies because it is very sensitive to observing slight changes in DNA conformation. (28) Due to its sensitivity, easy manipulation of studied samples, and relatively cheap, CD spectroscopy is regarded as a crucial complementary method in G4 studies; meanwhile, LTR-III G4's structure has only been resolved using NMR elucidation in K$^+$ solution, a typical hybrid conformation; and different G4 conformation has distinct CD spectra. So CD test was conducted to see if 477-albo will change the conformation of LTR-III G4. And noticeable conformation changes from a typical hybrid form into parallel form with the increase of 477-albo's concentration ratio were recorded (FIGS. 14A-14D).

Example 8-477-Albo Selectively Bind with DNA G4 while not RNA G4

Figure 15:
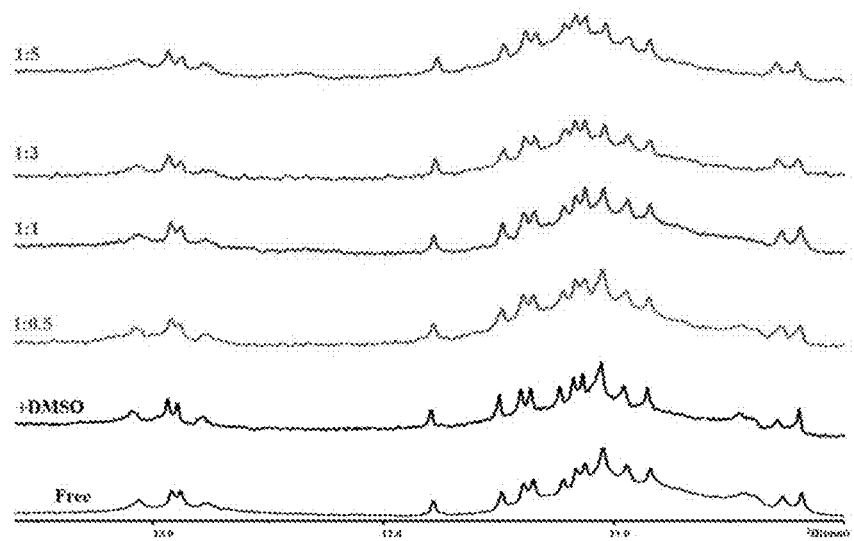
FIG. 15. Titration of 477-albo with HIV-1 U3 RNA G4. HIV-1 U3 RNA G4 has clear imino regions in the 1D $^1$H-NMR spectra, and that region did not change when titrated with 477-albo at the ratio of 1:0.5, 1:1, 1:3 and 1:5.
Figure 16:
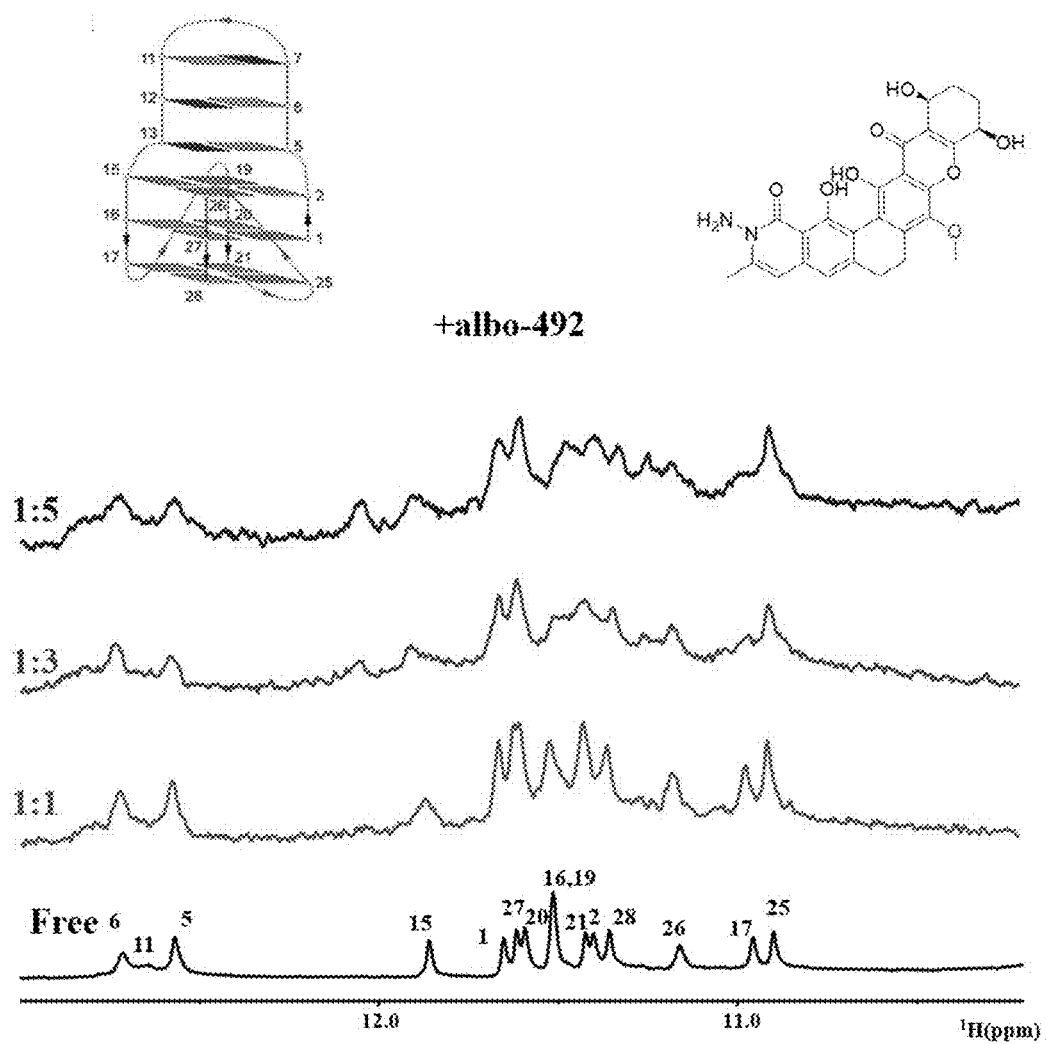
FIG. 16. Titration of 492-albo with HIV-1 LTR III G4.
Figure 17:
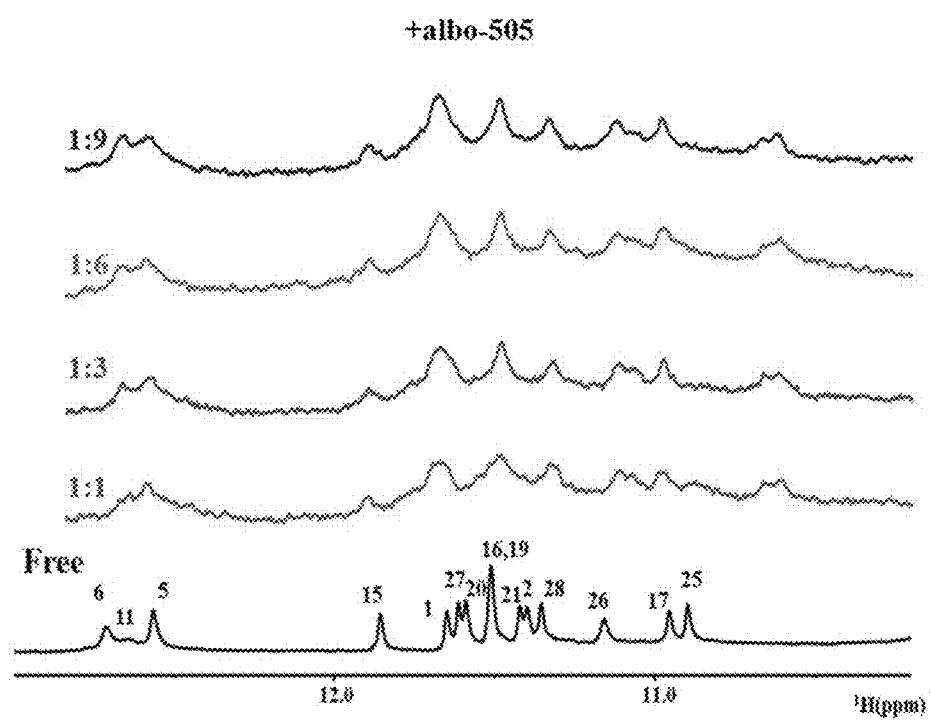
FIG. 17. Titration of 505-albo with HIV-1 LTR III G4.
Figure 18:
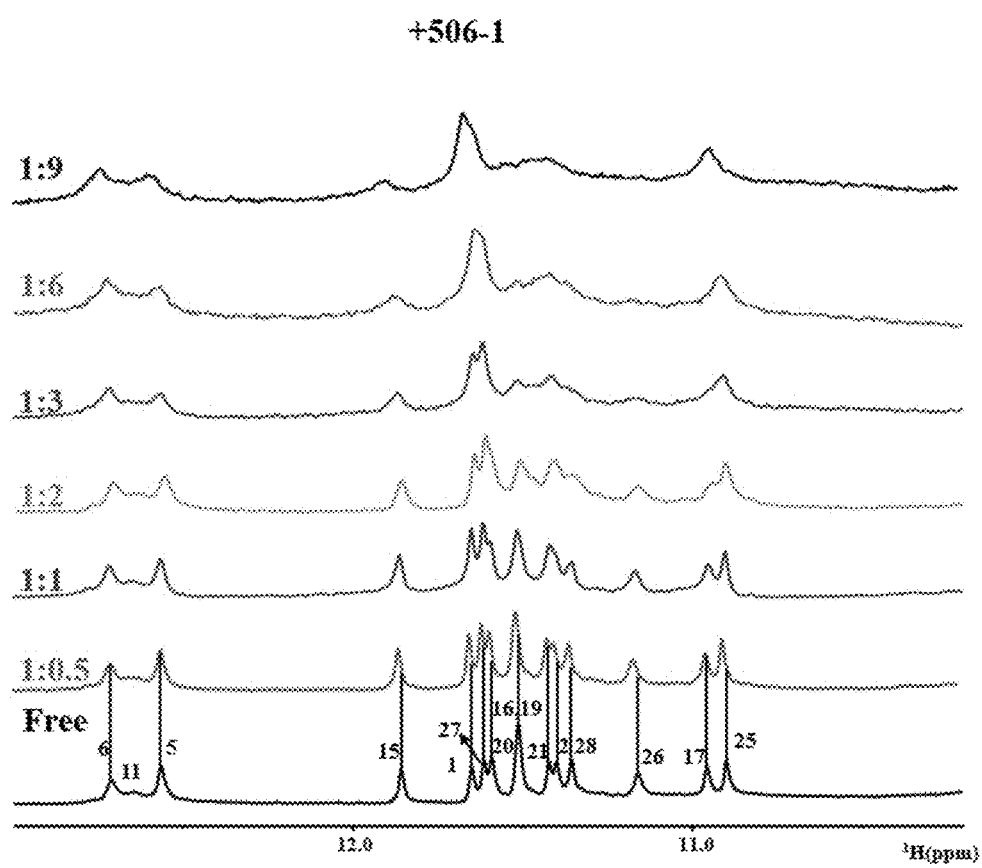
FIG. 18. Titration of 506-1-albo with HIV-1 LTR III G4.
Figure 19:
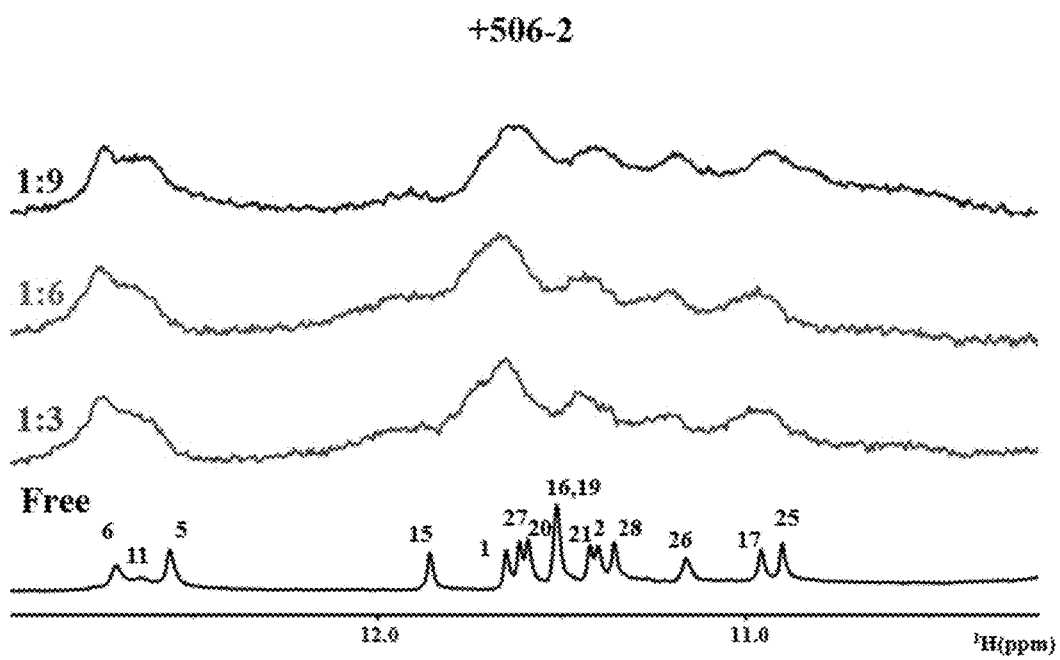
FIG. 19. Titration of 506-2-albo with HIV-1 LTR III G4.
Figure 20:
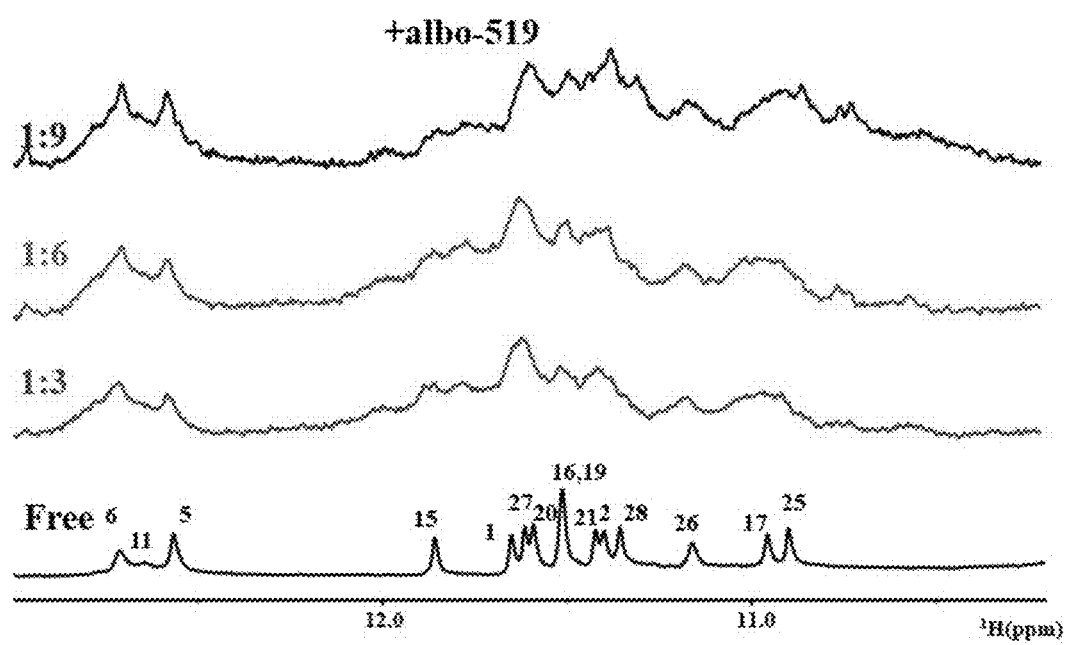
FIG. 20. Titration of 519-albo with HIV-1 LTR III G4.
Figure 21:
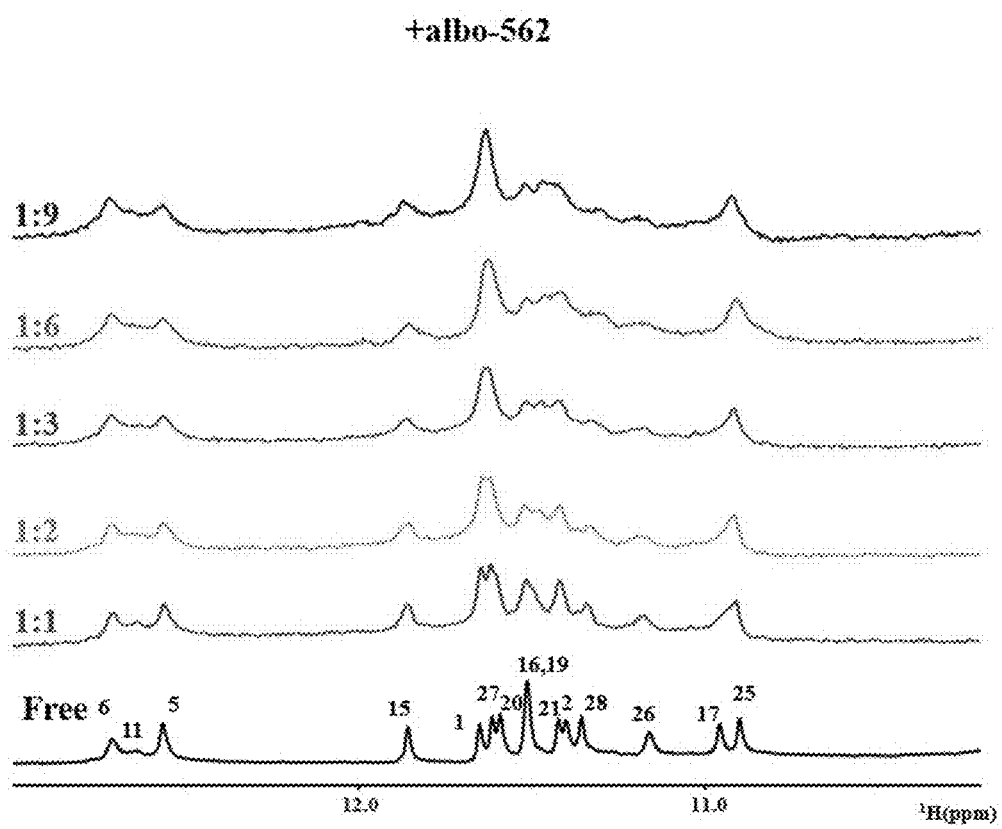
FIG. 21. Titration of 562-albo with HIV-1 LTR III G4.

Both DNA and RNA can form G4 structures, and RNA G4s are highly stable due to the existence of the 2'-hydroxyl group that will increase intramolecular hydrogen bonding. Previous studies have demonstrated that RNA G4s also play critical regulatory roles in translational regulation (29), 3' end processing (30), transcription termination, mRNA localization, and alternative splicing (31). In a word, RNA G4s also seem to be critical regulatory motifs of the transcriptome; Similar to the DNA region, the RNA counterpart can also form a parallel RNA G-quadruplex; in order to know if 477-albo has selectivity, we choose the U3 RNA region (which derives the identical LTR-III DNA region) to form U3 RNA G4 in vitro. The NMR titration experiment indicates 477-albo specific bind with LTR-III DNA G4 while not U3 RNA G4 (FIG. 15), indicates 477-albo has better selectivity than classical G4 ligand BRACO-19, which not only binds both DNA and RNA G4s of LTR-III but is also active against Epstein-Barr viruses (15) and human telomeric G4s (32).

Figure 22:
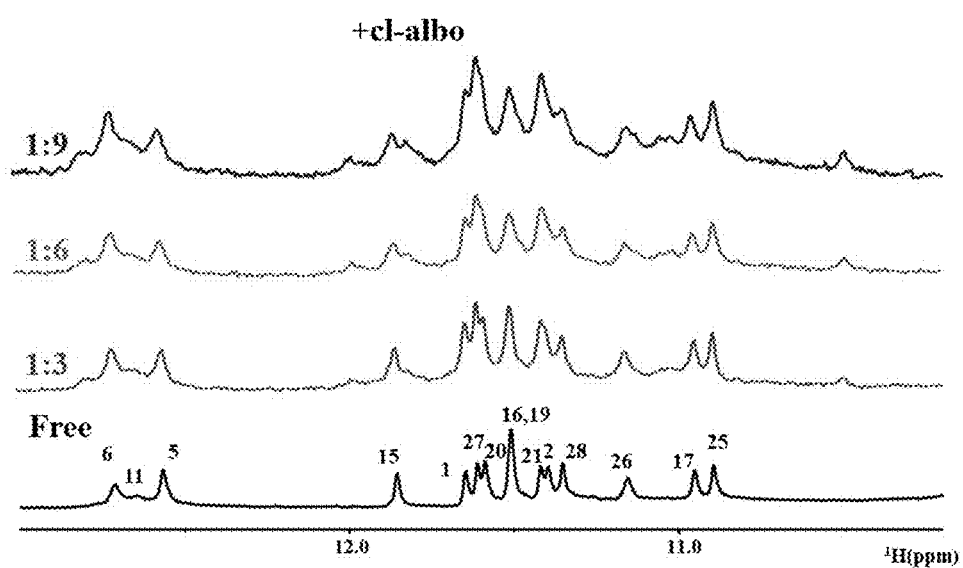
FIG. 22. Titration of chloroalbofungin with HIV-1 LTR III G4.

Example 9—The Comparison of Albofungin and its Derivatives in LTR III G-Quadruplex Binding Similar to albofungin, its derivatives 477-albo, 492-albo, 505-albo, 506-1-albo, 506-2-albo, 519-albo, and 562-albo also bind to LTR III G4 (FIGS. 16-22), while their binding affinities were much weaker than albofungin. Interestingly, chloroalbofungin, albofungin's monochlorinated analog, exhibits a poor binding affinity with LTR III G-quadruplex (FIG. 22).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES 1. worldwide website: un.org/zh/sections/issues-depth/aids/index.html.
2. worldwide website: wikipedia.org/wiki/HIV
3. Wlodawer, A. (2002) Rational approach to AIDS drug design through structural biology. *Annual Review of Medicine.* 53; 595-614.
4. De Clercq, E. (2013). The nucleoside reverse transcriptase inhibitors, nonnucleoside reverse transcriptase inhibitors, and protease inhibitors in the treatment of HIV infections (AIDS). *Advances in pharmacology,* 67, 317-358.
5. Hill, A., Sawyer, W., & Gazzard, B. (2009). Effects of first-line use of nucleoside analogues, efavirenz, and ritonavir-boosted protease inhibitors on lipid levels. *HIV clinical trials,* 10(1), 1-12.
6. Lv, Z., Chu, Y., & Wang, Y. (2015). HIV protease inhibitors: a review of molecular selectivity and toxicity. Hiv/aids (Auckland, NZ), 7, 95.
7. Imamichi, T. (2004). Action of anti-HIV drugs and resistance: reverse transcriptase inhibitors and protease inhibitors. *Current pharmaceutical design,* 10(32), 4039-4053.
8. Bochman, M. L., Paeschke, K., & Zakian, V. A. (2012). DNA secondary structures: stability and function of G-quadruplex structures. *Nature Reviews Genetics,* 13(11), 770-780.
9. Artusi, S., Nadai, M., Perrone, R., Biasolo, M. A., Palu, G., Flamand, L., . . . & Richter, S. N. (2015). The Herpes Simplex Virus-1 genome contains multiple clusters of repeated G-quadruplex: Implications for the antiviral activity of a G-quadruplex ligand. *Antiviral research,* 118, 123-131.
10. Murat, P., Zhong, J., Lekieffre, L., Cowieson, N. P., Clancy, J. L., Preiss, T., . . . & Tellam, J. (2014). G-quadruplexes regulate Epstein-Barr virus-encoded nuclear antigen 1 mRNA translation. *Nature chemical biology,* 10(5), 358-364.
11. Perrone, R., Butovskaya, E., Daelemans, D., Palu, G., Pannecouque, C., & Richter, S. N. (2014). Anti-HIV-1 activity of the G-quadruplex ligand BRACO-19. *Journal of Antimicrobial Chemotherapy,* 69(12), 3248-3258.
12. Ruggiero, E., & Richter, S. N. (2018). G-quadruplexes and G-quadruplex ligands: targets and tools in antiviral therapy. *Nucleic acids research,* 46(7), 3270-3283.
13. Piekna-Przybylska, D., Sullivan, M. A., Sharma, G., & Bambara, R. A. (2014). U3 region in the HIV-1 genome adopts a G-quadruplex structure in its RNA and DNA sequence. *Biochemistry,* 53(16), 2581-2593.
14. Perrone, R., Butovskaya, E., Daelemans, D., Palu, G., Pannecouque, C., & Richter, S. N. (2014). Anti-HIV-1 activity of the G-quadruplex ligand BRACO-19. *Journal of Antimicrobial Chemotherapy,* 69(12), 3248-3258.
15. Perrone, R., Nadai, M., Frasson, I., Poe, J. A., Butovskaya, E., Smithgall, T. E., . . . & Richter, S. N. (2013). A dynamic G-quadruplex region regulates the HIV-1 long terminal repeat promoter. *Journal of medicinal chemistry,* 56(16), 6521-6530.
16. Martinez, J. P., Sasse, F., Brönstrup, M., Diez, J., & Meyerhans, A. (2015). Antiviral drug discovery: broad-spectrum drugs from nature. *Natural product reports,* 32(1), 29-48.
17. She, W., Ye, W., Cheng, A., Liu, X., Tang, J., Lan, Y., . . . & Qian, P. Y. (2021). Discovery, Bioactivity Evaluation, Biosynthetic Gene Cluster Identification, and Heterologous Expression of Novel Albofungin Derivatives. *Frontiers in microbiology,* 12, 77.
18. Ye, W., She, W., Sung, H. Y., Qian, P., & Williams, I. D. (2020). Albofungin and chloroalbofungin: antibiotic crystals with 2D but not 3D isostructurality. *Acta Crystallographica Section C: Structural Chemistry,* 76(12), 1100-1107.
19. Butovskaya, E., Heddi, B., Bakalar, B., Richter, S. N., & Phan, A. T. (2018). Major G-quadruplex form of HIV-1 LTR reveals a (3+1) folding topology containing a stem-loop. *Journal of the American Chemical Society,* 140(42), 13654-13662.
20. Perrone, R., Butovskaya, E., Lago, S., Garzino-Demo, A., Pannecouque, C., Palb, G., & Richter, S. N. (2016). The G-quadruplex-forming aptamer AS1411 potently inhibits HIV-1 attachment to the host cell. *International journal of antimicrobial agents,* 47(4), 311-316.
21. Butovskaya, E., Soldà, P., Scalabrin, M., Nadai, M., & Richter, S. N. (2019). HIV-1 nucleocapsid protein unfolds stable RNA G-quadruplexes in the viral genome and is inhibited by G-quadruplex ligands. *ACS infectious diseases,* 5(12), 2127-2135.
22. Amrane, S., Kerkour, A., Bedrat, A., Vialet, B., Andreola, M. L., & Mergny, J. L. (2014). Topology of a DNA G-quadruplex structure formed in the HIV-1 promoter: a potential target for anti-HIV drug development. *Journal of the American Chemical Society,* 136(14), 5249-5252.
23. Geng, Y., Liu, C., Zhou, B., Cai, Q., Miao, H., Shi, X., . . . & Zhu, G. (2019). The crystal structure of an antiparallel chair-type G-quadruplex formed by Bromo-substituted human telomeric DNA. *Nucleic acids research,* 47(10), 5395-5404.
24. De Nicola, B., Lech, C. J., Heddi, B., Regmi, S., Frasson, I., Perrone, R., . . . & Phan, A. T. (2016). Structure and possible function of a G-quadruplex in the long terminal repeat of the proviral HIV-1 genome. *Nucleic acids research,* 44(13), 6442-6451.
25. Liu, C., Zhou, B., Geng, Y., Tam, D. Y., Feng, R., Miao, H., . . . & Zhu, G. (2019). A chair-type G-quadruplex structure formed by a human telomeric variant DNA in K+ solution. *Chemical science,* 10(1), 218-226.
26. Tosoni, E., Frasson, I., Scalabrin, M., Perrone, R., Butovskaya, E., Nadai, M., . . . & Richter, S. N. (2015). Nucleolin stabilizes G-quadruplex structures folded by the LTR promoter and silences HIV-1 viral transcription. *Nucleic acids research,* 43(18), 8884-8897.
27. Scalabrin, M., Frasson, I., Ruggiero, E., Perrone, R., Tosoni, E., Lago, S., . . . & Richter, S. N. (2017). The cellular protein hnRNP A2/B1 enhances HIV-1 transcription by unfolding LTR promoter G-quadruplexes. *Scientific reports,* 7(1), 1-13.
28. Kejnovski, Iva, et al. "CD Study of the G-Quadruplex Conformation." *G-Quadruplex Nucleic Acids. Humana,* New York, N.Y., 2019. 25-44.
29. S. Kumari, A. Bugaut, J. L. Huppert and S. Balasubramanian, *Nat. Chem. Biol.,* 2007, 3, 218
30. J. Christiansen, M. Kofod and F. C. Nielsen, *Nucleic Acids Res.,* 1994, 22, 5709
31. P. H. Wanrooij, J. P. Uhler, T. Simonsson, M. Falkenberg and C. M. Gustafsson, *Proc. Natl. Acad. Sci. U.S.A.,* 2010, 107, 16072
32. Neidle, S. (2010). Human telomeric G-quadruplex: The current status of telomeric G-quadruplexes as therapeutic targets in human cancer. *The FEBS journal,* 277(5), 1118-1125.

We claim:

1. A compound of formula (III), formula (IV), formula (V), formula (VI), or formula (VIII):

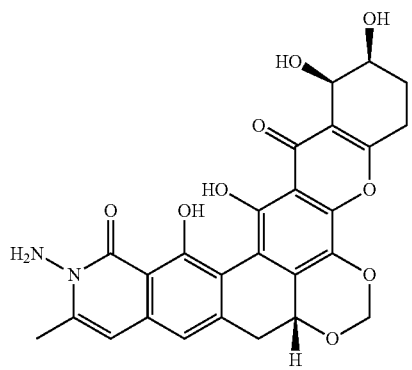

Formula (III)

506-1-Albo

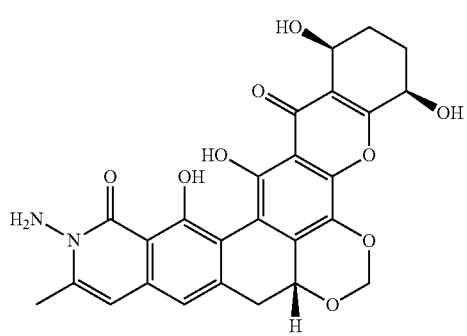

Formula (IV)

506-2-Albo

Formula (V)

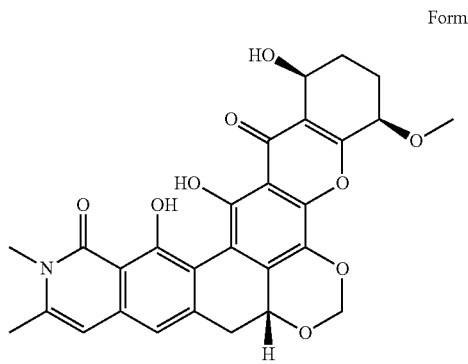

519-Albo

Formula (VI)

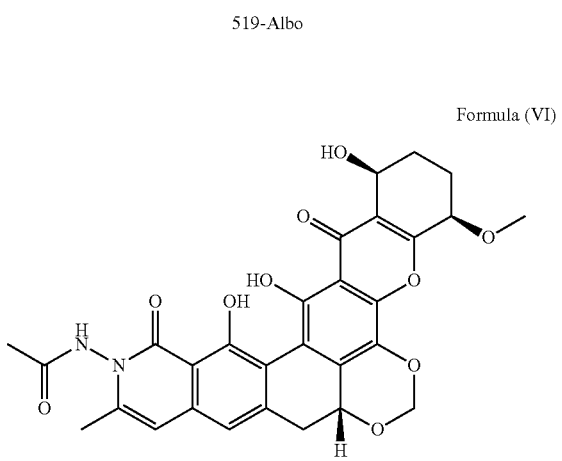

562-Albo

Formula (VIII)

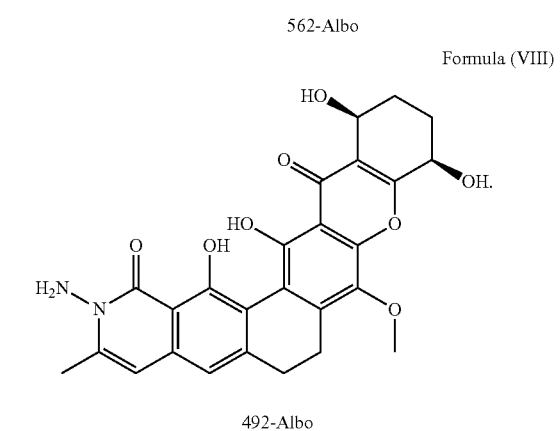

492-Albo

Formula (I)

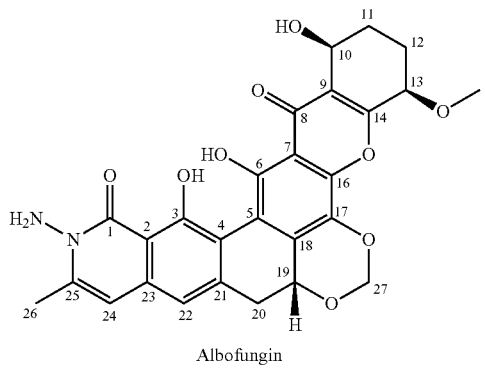

Albofungin

Formula (II)

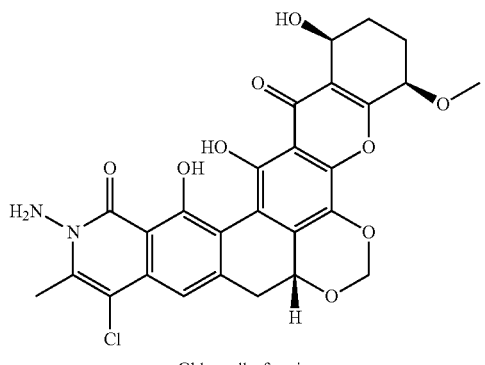

Chloroalbofungin

Formula (III)

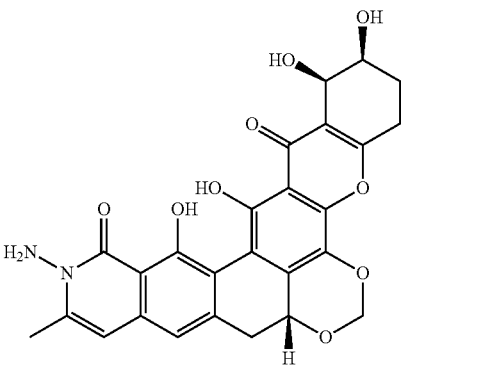

506-1-Albo

Formula (IV)

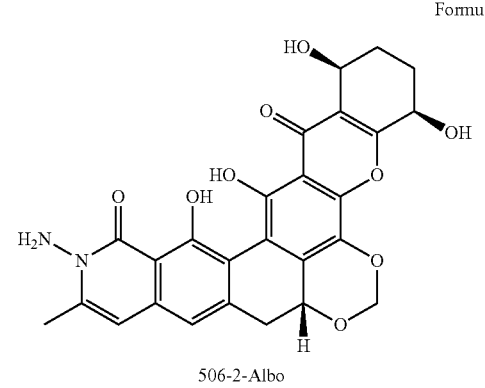

506-2-Albo

2. A composition comprising the compound of claim 1 and a pharmaceutically acceptable carrier and/or excipient.

3. A method of binding to a G-quadruplex (G4), the method comprising administering a compound of formula (I), formula (II), formula (III), formula (IV), formula (V), formula (VI), formula (VII), formula (VIII), or formula (IX), or combination thereof to a subject, wherein the subject is infected with human immunodeficiency virus (HIV), whereby the G4 is contacted and bound by the compound of formula (I), formula (II), formula (III), formula (IV), formula (V), formula (VI), formula (VII), formula (VIII), or formula (IX) or the combination thereof:

Formula (V)

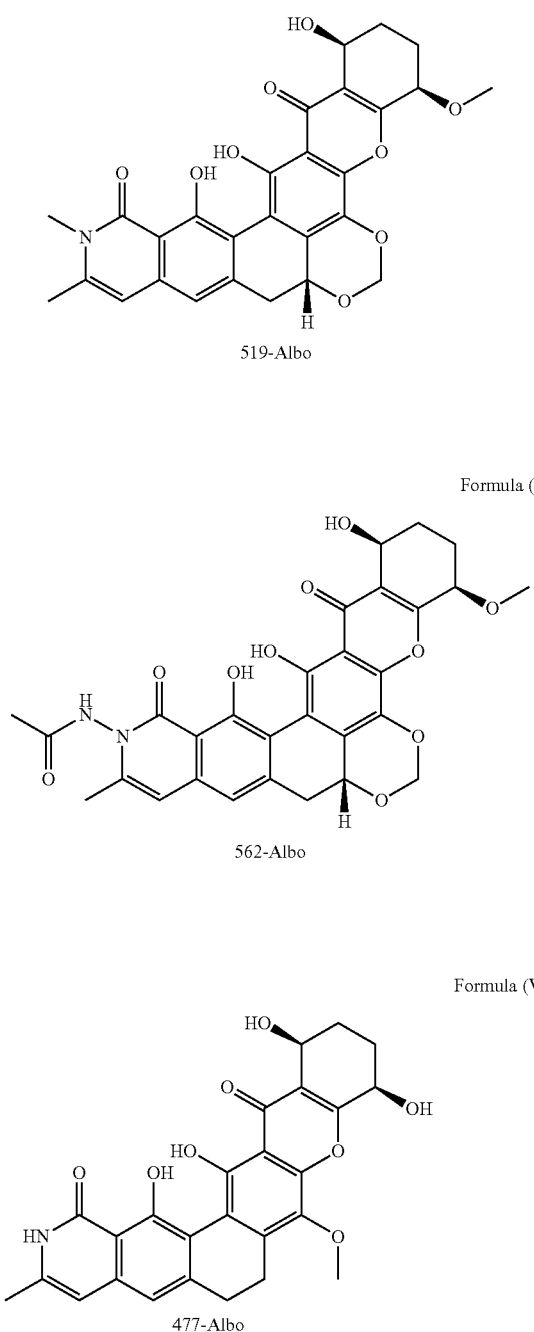

519-Albo

Formula (VI)

562-Albo

Formula (VII)

477-Albo

Formula (VIII)

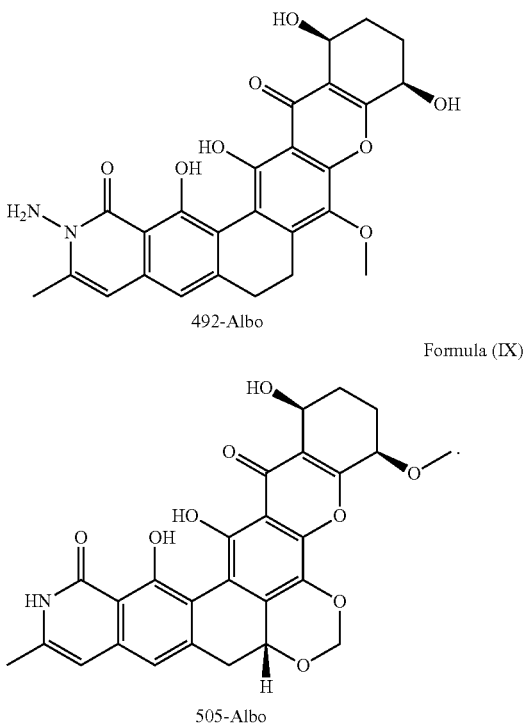

492-Albo

Formula (IX)

505-Albo

4. The method of claim 3, wherein a route of administration is oral administration.

5. The method of claim 3, wherein said compound or combination thereof contacts an HIV virion.

6. The method of claim 5, further comprising the compound of formula (I), formula (II), formula (III), formula (IV), formula (V), formula (VI), formula (VII), formula (VIII), or formula (IX), or a combination thereof entering or contacting an HIV-infected cell of the subject.

7. The method of claim 3, wherein the G4 is HIV-1 LTR-II G4, HIV-1 LTR-III G4, or HIV-1 LTR IV G4.

8. The method of claim 7, further comprising stabilizing HIV-1 LTR-II G4, HIV-1 LTR-III G4, or HIV-1 LTR IV G4.

9. The method of claim 7, further comprising stabilizing HIV-1 LTR-III G4.

10. The method of claim 3, wherein the HIV is HIV-1 or HIV-2.

11. The method of claim 3, wherein said compound of formula (I), formula (II), formula (III), formula (IV), formula (V), formula (VI), formula (VII), formula (VIII), or formula (IX), or combination thereof blocks viral replication.

12. The method of claim 11, wherein said compound of formula (I), formula (II), formula (III), formula (IV), formula (V), formula (VI), formula (VII), formula (VIII), or formula (IX), or combination thereof represses viral transcription initiation.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Homo sapiens

<400> SEQUENCE: 1
gggttagggt tagggtttgg g                                     21

<210> SEQ ID NO 2
<211> LENGTH: 33
<212> TYPE: DNA
<213> ORGANISM: Human immunodeficiency virus type 1

<400> SEQUENCE: 2
ggggactttc cagggaggcg tggcctgggc ggg                        33

<210> SEQ ID NO 3
<211> LENGTH: 28
<212> TYPE: DNA
<213> ORGANISM: Human immunodeficiency virus type 1

<400> SEQUENCE: 3
gggaggcgtg gcctgggcgg gactgggg                              28

<210> SEQ ID NO 4
<211> LENGTH: 19
<212> TYPE: DNA
<213> ORGANISM: Human immunodeficiency virus type 1

<400> SEQUENCE: 4
gggcgggact ggggagtgg                                        19